US011744199B2

(12) United States Patent
Daetwyler et al.

(10) Patent No.: US 11,744,199 B2
(45) Date of Patent: Sep. 5, 2023

(54) SELECTION BASED ON OPTIMAL HAPLOID VALUE TO CREATE ELITE LINES

(71) Applicant: Dow AgroSciences LLC, Indianapolis, IN (US)

(72) Inventors: Hans Dieter Daetwyler, Victoria (AU); Benjamin John Hayes, Victoria (AU); Kelly Robbins, Indianapolis, IN (US); Matthew James Hayden, Victoria (AU); German Spangenberg, Victoria (AU)

(73) Assignee: Corteva Agriscience LLC ( * ) Notice: Subject to any disclaimer, the term of this patent is extended or adjusted under 35 U.S.C. 154(b) by 0 days.

(21) Appl. No.: 16/127,813

(22) Filed: Sep. 11, 2018

(65) Prior Publication Data
US 2019/0021250 A1    Jan. 24, 2019

Related U.S. Application Data

(62) Division of application No. 14/586,488, filed on Dec. 30, 2014, now abandoned.

(60) Provisional application No. 62/092,737, filed on Dec. 16, 2014, provisional application No. 61/939,599, filed on Feb. 13, 2014, provisional application No. 61/922,148, filed on Dec. 31, 2013.

(51) Int. Cl.
A01H 1/04       (2006.01)
A01H 1/02       (2006.01)
C12Q 1/6895     (2018.01)
A01H 1/08       (2006.01)

(52) U.S. Cl.
CPC ............. A01H 1/04 (2013.01); A01H 1/02 (2013.01); A01H 1/08 (2013.01); C12Q 1/6895 (2013.01); C12Q 2600/13 (2013.01)

(58) Field of Classification Search
None
See application file for complete search history.

(56) References Cited

U.S. PATENT DOCUMENTS

| 2010/0100980 A1* | 4/2010 | Bull | A01N 57/20 800/278 |
|---|---|---|---|
| 2010/0138951 A1* | 6/2010 | Nelson | A01H 1/04 800/268 |
| 2010/0293673 A1 | 11/2010 | Bull | |
| 2012/0151625 A1* | 6/2012 | Guo | G16B 20/00 800/275 |

FOREIGN PATENT DOCUMENTS

| CN | 101528029 | 9/2009 |
|---|---|---|
| CN | 101802219 | 8/2010 |
| CN | 101970688 | 2/2011 |
| CN | 102224801 | 10/2011 |
| WO | 2007103786 | 9/2007 |
| WO | 2009029771 | 3/2009 |
| WO | 2009032724 | 3/2009 |

OTHER PUBLICATIONS

Jannink et al., 2010, Genomic selection in plant breeding: from theory to practice, Briefings in Functional Genomics 9: 166-177.*
Cole and VanRadden, 2011, Use of haplotypes to estimate Mendelian sampling effects and selection limits, Journal of Animal Breeding & Genetics 128: 446-455.*
Meuwissen et al., 2001, Prediction of total genetic value using genome-wide dense marker maps, Genetics 157: 1819-1829.*
Nirea et al., 2012, Strategies for implementing genomic selection in family-based aquaculture breeding schemes: double haploid sib test populations, Genetics Selection Evolution 44(30): 1-9.*
Murovec and Bohanec, Haploids and Doubled Haploids in Plant Breeding, 2012, In: Plant Breeding, Dr. Ibrokhim Abdurakhmonov (Ed.), ISBN: 978-953-307-932-5, InTech, pp. 87-107.*
Wagenast, T., et al. "Comparison of selection strategies and optimization criteria in hybrid maize breeding with doubled haploids." Maydica 54.2 (2009): 343. (Year: 2009).*
Barrett, J. C., et al., "Haploview: analysis and visualization of LD and haplotype maps," Bioinformatics Applications Note, 2005, pp. 263-265, vol. 21, No. 2.
Clark, Samuel A., et al., "The importance of information on relatives fro the prediction of genomic breeding values and the implications for the makeup of reference data sets in livestock breeding," Genetics Solution Evolution, 2012, 9 pages, vol. 44, No. 4.
Cole, J. B., et al., "Use of haplotypes to estimate mendelian sampling effects and selection limits,"Journal of Animal Breeding and Genetics, 2011, pp. 446-455, vol. 128.
Cole, J. B., et al., "Visualization of results from genomic evaluations," American Diary Sciences Association, 2010, pp. 2727-2740, vol. 93.
Daetwyler, Hans D., et al., "Slection on optimal haploid value increased genetic gain and preserves more genetic diversity relative to genomic selection," Genetics, Jun. 19, 2015, pp. 1341-1348, vol. 200, No. 4.
Frederic Hospital, "Selection in backcross programmes," Phil. Trans. R. Soc. B, 2005, pp. 1503-1511, vol. 360.
Frederic Hospital, "Size of donor chromosome segments around introgressed loci and reductions of linkage drag in marker-assisted backcross programs," Genetics, Jul. 2001, pp. 1363-1379, vol. 158.
International Search Report and Written Opinion; PCT?US2014/073075 dated Apr. 20, 2015.
Jannink et al.; Genomic selection in plant breeding: from theory to practice; Briefings in Functional Genomics, Feb. 15, 2010, vol. 9, No. 2, pp. 166-177.
Jannink, Jean-Luc, et al., "Genomic selection in plant breeding: from theory to practice," Briefings in Function Genomic, Feb. 15, 2010, pp. 166-177, vol. 9 No. 2.
Kemper, K. E., et al., "Long-term selection strategies for complex traits using high-density genetic markers," J. Dairy Sci, pp. 4646-4656, vol. 95.

(Continued)

Primary Examiner — Amjad Abraham
Assistant Examiner — Brian James Sullivan

(57) ABSTRACT

This disclosure concerns methods for estimating the breeding value of plants for the purpose of producing doubled haploid, for example, to identify selection candidates having high breeding values.

23 Claims, 19 Drawing Sheets

(56) References Cited

OTHER PUBLICATIONS

Lillehammer, Marie, "A low-marker density implementation of genomic selection in aquaculture using within-family genomic breeding values," Genetics Selection Evolution, 2013, 8 pages, vol. 45.

Lorenz, Aaron J., et al., "Resource allocation for maximizing prediction accuracy and genetic gain of genomic selection in plant breeding: A simulation experiment," Genes|Genomes|Genetics, Mar. 1, 2013, vol. 3, No. 3.

Lu et al., "Estimating breeding values using segments of chromosomes determined by lowest score criteria based on dense SNP data,".

Meuwissen, T. H. E., et al., "Prediction of total genetic value using genome-wide dense marker maps," Genetics, 2001, 1819-1829, vol. 157.

Nirea et al., "Strategies for implementing genomic selection in family-based aquaculture breeding schemes: double haploid sib test populations," Genetics, 2012, 9 pages, vol. 44.

Nirea et al., "Strategies for implementing genomic selection in family-based aquaculture breeding schemes: double haploid sib test populations," Oct. 30, 2012, 17 pages.

Odegard, et al., "Introgression of a major QTL from an inferior into a superior population using genomic selection," Genetics Selection Evolution, Jul. 27, 2009, 10 pages, vol. 41.

Odegard, J. et al., "Incorporating desirable genetic characteristics from an inferior into a superior population using genomic selection," Genetics, Feb. 2009, pp. 737-745, vol. 181.

Rober, F.K., et al., "in vivo haploid induction in maize—performance of new inducers and significance of doubled haploid lines in hybrid breeding," Maydica, 2005, pp. 275-283.

Tanksley, Steven D., "Molecular markers in plant breeding," Plant Molecular Biology Reporter, 1983, pp. 3-8, vol. 1.

Visscher, Peter M., et al., "Marker-assisted introgression in backcross breeding programs," Genetics, Dec. 1996, 1923-1932, vol. 144.

Yi, Nengjun et al., "Bayesian model choice and search strategies for mapping interaction quantitative trait loci," Genetics, Oct. 2003, pp. 867-883, vol. 165.

\* cited by examiner

SELECTION BASED ON OPTIMAL HAPLOID VALUE TO CREATE ELITE LINES

CROSS-REFERENCE TO RELATED APPLICATION

This application is a divisional application of U.S. patent application Ser. No. 14/586,488 filed on Dec. 20, 2014, which claims the benefit of U.S. Provisional Patent Application Ser. No. 61/922,148, filed Dec. 31, 2013, U.S. Provisional Patent Application Ser. No. 61/939,599, filed Feb. 13, 2014, and U.S. Provisional Patent Application Ser. No. 62/092,737, filed Dec. 16, 2014, each of the disclosures of which is hereby incorporated herein in their entirety by this reference.

FIELD OF THE DISCLOSURE

The present disclosure relates to plant molecular genetics and breeding. Some embodiments relate to methods for making selections in a breeding population for preferred mating pairs. Some embodiments relate to methods for selecting a progeny plant for use and/or advancement as an elite line.

BACKGROUND

The creation of doubled haploids in plant breeding programs allows for the creation of completely homozygous individuals from outbred plants, thereby facilitating the development of new varieties. Choosing the best doubled haploid is accomplished by the time-consuming and expensive process of artificial phenotypic selection, utilizing phenotypic records of individual plants and their relatives. In some cases, phenotypic selection may also involve progeny testing. Furthermore, methods that combine phenotypes and pedigrees can be used to predict an individual's estimated breeding value (EBV). These EBVs may include information on progeny performance from multiple matings of the individual. See, e.g., Schaeffer (2006) J. Anim. Breed. Genet. 123:218-23. Generally, selection based on EBVs, which are calculated with best linear unbiased prediction (BLUP), is advantageous when compared to using only phenotypes because the information obtained from relatives increases the reliability of the estimate. Henderson (1975) Biometrics 31:423-447.

Genomic selection (GS) is currently being implemented to improve plant selection efficiency. It is a statistical genetic evaluation method that uses both phenotypic (e.g., trait observations, such as disease resistance and quality attributes) and genomic data. Meuwissen et al. (2001) Genetics 157:1819-29. GS results in trait effect estimates for all markers in a particular population. In GS, trait effect estimates can be added to produce a genomic estimated breeding value (GEBV) for an individual. A reference population with phenotypes and genotypes, where marker effects are estimated, is used to derive a "prediction equation." This prediction equation can then be applied to genotyped individuals to predict a GEBV.

The usual implementation of genomic selection requires a reference population with phenotypes and genotypes where marker effects are estimated, the so-called prediction equation. However, information for GS from a sparse marker map in an outbreeding species is limited, because the linkage phase between particular markers and QTLs must be established for every family in which the marker is to be used for selection. Also, some markers in a dense marker map will be very close to the QTL, and thus be in linkage disequilibrium with the QTL. Hastbacka et al. (1992) Nat. Genet. 2:204-11. Furthermore, there will be many loci in marker maps that have no genetic variance (i.e., are not segregating), greatly outnumbering those that do display genetic variance.

In GS methods, selection limits for a population have been estimated by assuming that either whole chromosome haplotypes or individual alleles can be selected and combined as necessary to produce new complete genomes (e.g., an "ultimate animal" whose genome includes all of the best chromosomes in a population). Cole and VanRaden (2011) J. Anim. Breed. Genet. 128:446-55. In addition, in silico selection programs may similarly make use of genetic algorithms to breed an "ultimate cow" that contains the best known chromosome segments. Kemper et al. (2012) J. Dairy Sci. 95:4646-56.

In cattle, whole chromosome GEBVs may be used to identify preferred mating partners (Cole and VanRaden (2010) J. Dairy Sci. 93:2727-40), while in fish, simulation may be useful to increase predictive accuracy by exploiting certain combinations of doubled haploids ("extreme genotypes") in the reference population (Nirea et al. (2012) Genetics Selection Evolution 44:30). However, antagonistic relationships among both major and minor QTLs prevent GEBV from reaching calculated selection limits. See, e.g., Cole and VanRaden (2011), supra. Furthermore, selection based on estimated breeding values maximizes genetic gain in the next generation at the expense of genetic diversity. Kemper et al. (2012), supra. Thus, selection based on overall GEBV gives the highest response in the next generation, but it is not guaranteed to maximize gains over multiple generations.

An individual's genomic breeding value is the sum of all allele effects, and improvement in a complex trait requires favorable changes to allele frequencies for many distinct loci. However, the doubled haploids produced in a plant breeding program will vary, because each individual inherits a different combination of haplotypes.

BRIEF SUMMARY OF THE DISCLOSURE

For the purpose of breeding existing plant varieties to produce a new variety, certain combinations of haplotypes will be superior to others, as they combine the best alleles in an individual plant. Embodiments herein utilize a novel plant breeding strategy that incorporates the selection of optimal or near-optimal haplotypes (e.g., genome segment haplotypes) in a process for the production and selection of elite doubled haploid individuals. In embodiments, the genomic optimal haploid value (OHV), which is the value of the best haploid genome that could be produced from a segregating plant, is determined for a segregating individual or for an individual candidate for a breeding pair (or potential breeding pair). In some examples, the OHV is determined by making genomic predictions for individual haploid genome segments, identifying the best haploid genome segment (i.e., the segment with the highest predicted value) for each pair of segments in a diploid, and combining (e.g., summing) the values of these best segments over all segments, thereby arriving at the breeding value of the haploid individual having the best combination of genome segments; i.e., the OHV. In examples, the aggregate breeding value of a doubled haploid individual with two copies of each best genomic segment is twice (2×) the OHV.

In certain embodiments, one or more haploid plants or haploid tissues are produced from a segregating plant. The combined haploid value (CHV) is determined for each of the haploid plant or haploid tissues, which CHV is the sum of breeding values (e.g., for a quantitative trait of interest) for segments of the haploid genome ("haploid values;" HVs). In particular embodiments, the CHV of each haploid plant or tissue is compared to the OHV of the segregating plant. In some examples, if the CHV approaches the OHV, the haploid plant or tissue is selected, which selected haploid plant or tissue may then be used to make a doubled haploid plant.

In some embodiments, the OHV of each plant in a plurality of plants is compared with the OHV of the other plant(s) in the plurality, and is used as a criterion for selection of an "optimal" cross. Thus, one or more individuals having an OHV that is greater than others may be selected for breeding based on their potential to produce the best haploid chromosome set that can be used to generate a doubled haploid, thereby introducing a selection step prior to breeding or the generation of the doubled haploid population. In some further embodiments, the selected individual(s) are crossed with another plant to produce progeny plants (e.g., $F_1$, $F_2$, or $F_3$ progeny plants), and the OHV of at least one progeny plant is determined. If the OHV of the progeny plant is greater than others, the progeny plant can be selected for selfing or to produce haploids.

In some embodiments, haploid plant or haploid tissue is produced from a selected progeny plant, and the CHV of the haploid plant or tissue is compared to the OHV of the selected progeny plant. In some examples, if the CHV approaches the OHV, the haploid plant or tissue is further selected, which further selected haploid plant or tissue may then be used to make a doubled haploid plant.

In some embodiments, the foregoing methods of selection increase genetic gain and genetic diversity when compared to GS. Thus, OHV selection may allow for increased genetic gain over multiple generations in a breeding program, when compared to what is obtainable by GS.

Some embodiments herein provide OHV selection methods for producing an elite doubled haploid plant. In particular embodiments, the method comprises determining the genomic OHV for an individual plant, producing a population of haploids (and/or doubled haploids thereof) from the individual, and selecting an elite plant from the population for a CHV equaling or approaching the OHV.

Also provided in some embodiments herein are OHV selection plant breeding methods that comprise evaluating the potential of a line cross to produce an elite double haploid, possibly containing a desirable allele or GM event, which then can be selected for further breeding. In some embodiments, the method comprises determining the optimal genomic OHV for potential progeny of a first and at least a second plant, and crossing the first and second plant if the optimal OHV satisfies a selection criterion. In particular embodiments, the criterion is the condition of the optimal OHV being the highest of those determined for the potential progeny of the first plant with a plurality of additional plants. Thus, in some examples, the method comprises determining the highest possible genomic OHV for potential progeny of a first plant and each of a plurality of additional plants, and crossing the first plant with the member of the plurality that yields the highest possible OHV in a potential cross with the first plant.

Also provided in some embodiments herein are OHV selection methods for producing an elite doubled haploid plant, wherein the method comprises crossing a first and a second plant to produce a population of progeny plants, producing a population of haploids (and optionally doubled haploids thereof) from at least one of the progeny plants, and selecting an elite doubled haploid plant or haploid for the production of an elite doubled haploid plant. In some examples, the population of haploids is produced from a progeny plant that is selected for an OHV that approaches the optimal OHV for the breeding cross. In some examples, the haploid for the production of an elite doubled haploid plant is selected from the population of haploids for a CHV that approaches the OHV. In particular embodiments, the first plant comprises an allele or transgenic event that is introgressed into the elite doubled haploid plant or haploid for the production of an elite doubled haploid plant.

In some embodiments herein, a method for producing an elite doubled haploid plant is performed over multiple steps in a plant breeding program. For example, a first plant line may be used to produce an elite doubled haploid using OHV selection, which elite doubled haploid becomes a second plant line. The second plant line may then be used again for crossing. The progeny of these crosses may then again be selected based on OHV to produce a second elite doubled haploid. This process may be repeated as many times as is within the discretion of the skilled artisan, in order to obtain a new, desirable elite plant line.

Utilization of OHV in a plant breeding program in some embodiments increases genetic gain over GS (for example, by up to 0.6 genetic base standard deviations (SD)), while also increasing genetic diversity when compared to GS. Larger increases in genetic gain may be realized by increasing the number of progeny produced and genotyped for each breeding pair. Advantages of OHV can be realized at no additional cost, assuming the scale of DH production remains constant, thus making OHV selection an attractive new tool for the plant breeder.

Also described herein are plant selection systems comprising a kit for determining the genotype(s) of one or more plants; a database; means for determining a OHV from the genotype(s); and a user interface allowing a user to input genotype information, wherein the system determines a OHV for the one or more plants. In particular embodiments, the kit comprises a solid support having polynucleotides bound thereto, wherein each polynucleotide hybridizes to a polymorphic genetic marker that is tightly linked to a genome segment haplotype. In particular embodiments, the kit comprises a PCR-based assay. In particular embodiments, the kit is used to genotype a half seed or very young plant, and/or material from a haploid plant. In some examples, the means for determining an OHV from the genotype(s) is analytical programming. In some examples, the means for determining an OHV from the genotype(s) is a reference chart.

The foregoing and other features will become more apparent from the following detailed description of several embodiments, which proceeds with reference to the accompanying figures.

DETAILED DESCRIPTION

I. Overview of Several Embodiments

Figure 1:
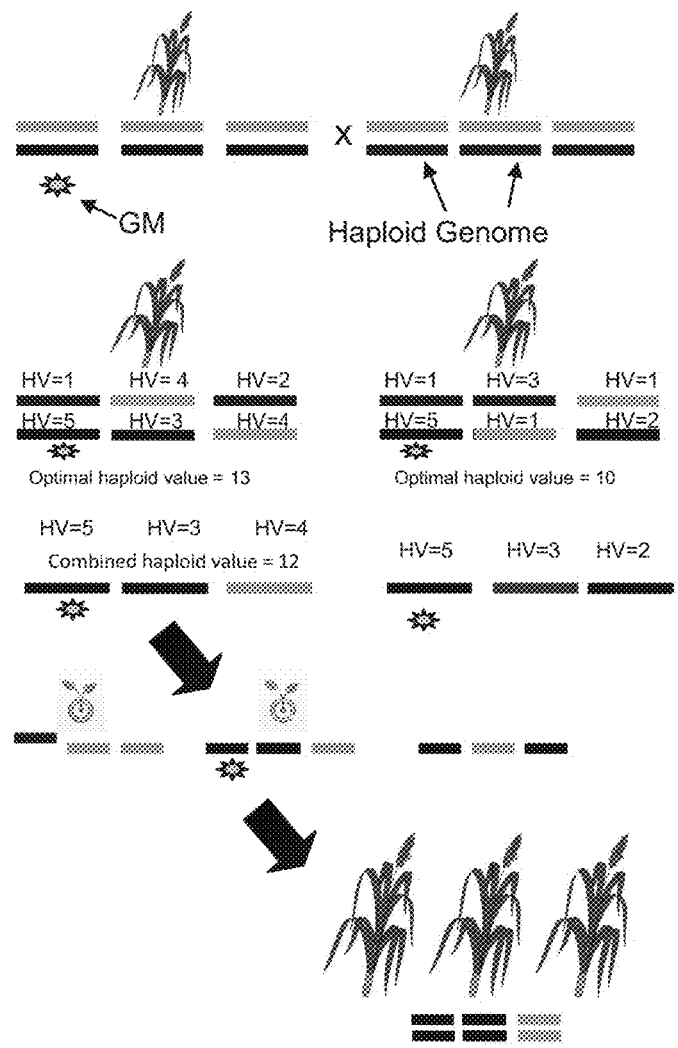
FIG. 1 includes an example of applying OHV selection in the development of a new wheat variety. In the first step of this example, HVs for a desired trait are estimated for each haploid genome segment in a first plant line with a desirable trait (i.e., a GM event, represented by the star) and a second plant line that is a breeding partner of the first plant. In silico, the optimum haploid value (OHV; the best doubled haploid that could be produced from a segregating plant, which is in this case progeny of the cross) is determined. In the illustrated example, the OHV is determined for two progeny plants, and the highest OHV is 5+4+4=13. In the next step, CHVs for the trait are determined for haploids generated from the segregating progeny of the cross having the highest OHV. In this example, a haploid plant having a CHV that approaches the highest OHV (i.e., CHV=12) is selected. In the third step, doubled haploids are created from this haploid plant, which doubled haploid is selected as a new elite variety.

In embodiments herein, an optimum double haploid (i.e., having a haploid value approaching the "OHV") is determined using value predictions for individual haploid genome segments (such as may be found in a haploid or gamete of a line cross), identifying the best genome segments for each pair for a trait of interest, and summing these. The highest possible OHV of a line cross is a different value measurement than the GEBV of the cross. For example, a line cross may yield one very good haploid chromosome and one very poor haploid chromosome at a given chromosome pair. In such an instance, the GEBV would give the average of these values, while the OHV as described herein reflects the value of combining very good haploid alleles.

The GEBV is the sum of all allele effects, so if an individual carries unfavorable alleles, it will reduce their GEBV. GS will tend towards increasing the total frequency of the haplotype in the population (i.e., homozygosity). In contrast, OHV sums only the best haplotype value in each segment, and therefore it will ignore low merit alleles if the other haplotype at the segment is superior. There is no additional benefit to carrying two favorable haplotypes, as the individual's OHV will remain the same. This maintains a more diverse set of haplotypes in the breeding population, and leads to a substantive and striking increase in diversity from OHV selection. The haplotypes maintained may be inferior, because they carry a number of unfavorable QTL alleles, but such haplotypes can also include one or more favorable alleles. Over time recombination may "release" such favorable alleles into an average or favorable background, and then these haplotypes may be increased in frequency by selection.

Demonstrated herein is the surprising result that not only does OHV selection alone provides, for example, up to 0.6 genetic SD in additional genetic gain over GS. OHV selection also preserves more genetic diversity in the breeding population, which provides greater flexibility and enables more genetic gain in the long-term. For example, OHV selection in particular embodiments decreases the possibility of guiding a breeding population into a scenario where a loss of genetic variance after several rounds of selection prevents or limits further improvement of the trait (i.e., a genetic "dead end").

A further advantage of OHV selection is that elite plants may be chosen based on their potential to produce a favorable (e.g., best) doubled haploid, which introduces an additional selection step before doubled haploids are created, leading to cost savings and advantages in performance. This innovation accelerates the development of cultivars with desirable alleles or transgenic events in optimized genetic backgrounds. A particular advantage of OHV selection is that an individual's real value in a breeding program can be accurately predicted before it exhibits a phenotype (e.g., in a juvenile plant, embryo, or tissue), and/or before the plant is crossed. Early selection decisions in a breeding program offer significant savings in time and growing costs, as inferior individuals may be identified and eliminated before they consume valuable resources.

In some embodiments, OHV selection takes into account additive and epistatic effects. The evaluation of epistatic interactions in the breeding of new, superior plant varieties is currently highly impractical, due to the immense number of possible pairwise combinations of single nucleotide polymorphisms across the subject genome. In particular embodiments herein, the evaluation of epistatic interactions is greatly facilitated by reducing the number of epistatic interactions to be tested. For example, loci by loci interactions may be tested using haploid genome segments, such as are used to determine HV, CHV, and OHV. By way of further example, interactions at longer genomic distances may be evaluated by testing interactions of the most common haplotypes of whole haploid genome segments. Inclusion of epistatic effects according to the foregoing strategies allows in particular embodiments for improved selection of favorable interactions and genetic backgrounds in plant breeding.

We have described and tested in silico a new breeding framework (OHV) that optimizes the selection of lines that result in elite doubled haploids. OHV selection results in more genetic gain than GS, and this advantage grows over time. The focus on haplotype selection allows OHV selection to carry substantially more genetic diversity in the breeding population.

II. Abbreviations

BLUP best linear unbiased prediction
cM centimorgan
CHV combined haploid value
EBV estimated breeding value
GEBV genomic estimated breeding value
GM genetically modified
GS genomic selection
HV haploid value
LD linkage disequilibrium
OCV optimal cytoplasmic value
OHV optimal haploid value
PCR polymerase chain reaction
QTL quantitative trait locus
SD standard deviation

III. Terms

Optimal: As used herein in the context of haplotype values, the term "optimal" may refer to a prediction of the highest CHV obtainable for a segregating plant (i.e., the OHV). In some examples, haploids are created from a segregating plant (e.g., progeny of a cross), and HVs are determined for genomic segments in the resulting haploids, which HVs are summed to yield the CHV. In some examples, an individual haploid is selected that has a CHV that approaches the OHV. For example, an individual may be selected that has an CHV that is the same, or substantially the same, as the OHV. By way of further example, a CHV that approaches the OHV may be the closest CHV to the OHV that is determined in the population. In some embodiments, if an individual is not identified that has a CHV that is close enough to the OHV to warrant selection in the estimation of the skilled practitioner, further progeny may be produced from the specific cross until an individual is identified and selected.

Population: As used herein, the term "population" refers to a group of individuals that potentially breed with each other, such that they contribute genetically to the next generation, including but not limited to those individuals in a plant breeding program. Such a group may be of any size (e.g., a species, breed, line, cultivar, or progeny of a single or multiple cross(es)).

Breeding value: As used herein, the term "breeding value" refers to the genetic value of an individual as a parent in a breeding program, and to the effect of an individual's genes or genetic markers when considered in isolation or combination (i.e., "aggregate breeding value") on performance against a selection criterion or criteria.

Genetic gain: As used herein, the term "genetic gain" refers to the average change in a heritable trait or combination of heritable traits from one generation to the next generation, including a predicted genetic gain and/or an actual genetic gain. In some embodiments, the genetic gain advances values for the heritable trait(s) in the direction of one or more selection targets, or at least avoids significant negative genetic gain (i.e., an adverse effect for the selection criteria).

Outbred: As used herein, the term "outbred" refers to an individual produced by reproduction between genetically dissimilar parents. In contrast, the term "inbred" refers to an individual produced by reproduction between genetically similar, or identical, parents. In practice, a plant breeder utilizing an outbred population generally has limited information about the genetic characteristics of individuals (e.g., what genes they carry, and how heterozygous they are). Moreover, background genetic data is often unreliable, because it can change rapidly.

Cross: The terms "breeding cross," "cross," and "crossing" are used interchangeably herein, and refer to the interbreeding of individuals that are distantly related or closely related (e.g., backcrossing, inbreeding, or selfing), such as deliberate breeding in a plant breeding program. Progeny of a cross refers to one or more descendants of a cross and may include, for example, $F_1$, $F_2$, $F_3$ and progeny of a subsequent generation.

Backcrossing: Backcrossing methods may be used to introduce a nucleic acid sequence into plants. The backcrossing technique has been widely used for decades to introduce new traits into plants. Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent. In some embodiments herein, a backcross breeding program incorporates OHV selection, for example, to provide an additional selection step to identify a preferred recurrent parent.

Locus: As used herein, the term "locus" refers to a position on the genome that corresponds to a discernible or measurable characteristic (e.g., a trait). An SNP locus is defined by a probe that hybridizes to DNA contained within the locus.

Epistasis: As used herein, the term "epistasis" (or "epistatic") refers to an interaction between two or more loci. An epistatic interaction is one in which the expression of one gene depends on the presence of one or more additional genes. For example, if two epistatic genes "A" and "B" are mutated, and each mutation by itself produces a unique phenotype, but the two mutations together show the same phenotype as the gene A mutation, then gene A is epistatic to gene B.

Allele: As used herein, the term "allele" refers to any one of the different forms of a gene or DNA sequence at a single locus.

Marker: As used herein, a marker refers to a gene or nucleotide sequence that can be used to identify plants (e.g., haploid and diploid) that are likely to have a particular allele and/or exhibit a particular trait or phenotype. A marker may be described as a variation at a given genomic locus. A genetic marker may be a short DNA sequence, such as a sequence surrounding a single base-pair change (single nucleotide polymorphism, or "SNP"), or a long sequence, for example, a minisatellite/simple sequence repeat ("SSR"). A "marker allele" refers to the version of the marker that is present in a particular plant. The term marker as used herein may refer to a cloned segment of plant chromosomal DNA, and may also or alternatively refer to a DNA molecule that is complementary to a cloned segment of plant chromosomal DNA. In particular embodiments, the identification of a marker in a plant facilitates the determination of a breeding value for a particular genomic segment, which value may be combined with other values to yield an HV.

In some embodiments, the presence of a marker in a plant may be detected through the use of a nucleic acid probe. A probe may be a DNA molecule or an RNA molecule. RNA probes can be synthesized by means known in the art, for example, using a DNA molecule template. A probe may contain all or a portion of the nucleotide sequence of the marker and additional, contiguous nucleotide sequence from the plant genome. This is referred to herein as a "contiguous probe." The additional, contiguous nucleotide sequence is referred to as "upstream" or "downstream" of the original marker, depending on whether the contiguous nucleotide sequence from the plant chromosome is on the 5' or the 3' side of the original marker, as conventionally understood. As is recognized by those of ordinary skill in the art, the process of obtaining additional, contiguous nucleotide sequence for inclusion in a marker may be repeated nearly indefinitely (limited only by the length of the chromosome), thereby identifying additional markers along the chromosome. The number of probes utilized in particular examples may be determined according to the discretion of the skilled practitioner, for example, depending upon the number of loci or QTLs being screened.

An oligonucleotide probe sequence may be prepared synthetically or by cloning. Suitable cloning vectors are well-known to those of skill in the art. An oligonucleotide probe may be labeled or unlabeled. A wide variety of labels and labeling techniques exist for nucleic acid molecules, including, for example and without limitation: Radiolabeling (e.g., by nick translation, random priming, and tailing with terminal deoxytransferase); fluorophores; enzymes; enzyme substrates; enzyme cofactors; and enzyme inhibitors.

A probe may contain a nucleotide sequence that is not contiguous to that of the original marker; this probe is referred to herein as a "noncontiguous probe." The sequence of the noncontiguous probe is located sufficiently close to the sequence of the original marker on the chromosome so that the noncontiguous probe is genetically linked to the same marker or gene as the original marker. For example, in some embodiments, a noncontiguous probe is located within 100 cM; 95 cM; 90 cM; 85 cM; 80 cM; 75 cM; 70 cM; 65 cM; 60 cM; 55 cM; 50 cM; 45 cM; 40 cM; 35 cM; 30 cM; 25 cM; 20 cM; 15 cM; or 10 cM of the original marker on the chromosome. In some examples, a noncontiguous probe is located within about 50 cM of the original marker.

A probe may be an exact copy of a marker to be detected. A probe may also be a nucleic acid molecule comprising, or consisting of, a nucleotide sequence that is substantially identical to a cloned segment of chromosomal DNA comprising a marker to be detected.

A probe may also be a nucleic acid molecule that is "specifically hybridizable" or "specifically complementary" to an exact copy of the marker to be detected ("DNA target"). "Specifically hybridizable" and "specifically complementary" are terms that indicate a sufficient degree of complementarity such that stable and specific binding occurs between a nucleic acid molecule (e.g., an oligonucleotide) and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tij ssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, N Y, 1993; and Ausubel et al., Eds., *Current Protocols in Molecular Biology*, Chapter 2, Greene Publishing and Wiley-Interscience, N Y, 1995.

As used herein, "stringent conditions" encompass conditions under which hybridization will only occur if there is less than 25% mismatch between the hybridization molecule and the DNA target. "Stringent conditions" include further particular levels of stringency. Thus, as used herein, "moderate stringency" conditions are those under which molecules with more than 25% sequence mismatch will not hybridize; conditions of "medium stringency" are those under which molecules with more than 15% mismatch will not hybridize; and conditions of "high stringency" are those under which sequences with more than 10% mismatch will not hybridize. Conditions of "very high stringency" are those under which sequences with more than 6% mismatch will not hybridize.

In particular embodiments, stringent conditions are hybridization at 65° C. in 6× saline-sodium citrate (SSC) buffer, 5×Denhardt's solution, 0.5% SDS, and 100 µg sheared salmon testes DNA, followed by 15-30 minute sequential washes at 65° C. in 2×SSC buffer and 0.5% SDS, followed by 1×SSC buffer and 0.5% SDS, and finally 0.2×SSC buffer and 0.5% SDS.

With respect to all probes discussed, supra, the probe may comprise additional nucleic acid sequences, for example, promoters; transcription signals; and/or vector sequences.

Linked: Linked, tightly linked, and extremely-tightly linked genetic markers may be useful in marker-assisted breeding programs, for example and without limitation, to introgress a desirable trait or phenotype into a plant variety; and to determine a haplotype (e.g., for HV determination) for a genomic segment in a chromosome of an individual or theoretical individual (e.g., a possible individual progeny, as is predicted to be produced by a cross of parent plants).

As used herein, linkage between genes or markers refers to the phenomenon in which genes or markers on a chromosome show a measurable probability of being passed on together to individuals in the next generation. The closer two genes or markers are to each other, the closer to (1) this probability becomes. Thus, the term "linked" may refer to one or more genes or markers that are passed together with a second gene or marker with a probability greater than 0.5 (which is expected from independent assortment where markers/genes are located on different chromosomes). Because the proximity of two genes or markers on a chromosome is directly related to the probability that the genes or markers will be passed together to individuals in the next generation, the term "linked" may also refer herein to one or more genes or markers that are proximate to one another on the same chromosome.

As used herein, linkage between markers and desirable traits or phenotypes may refer to one or more markers that are each passed together with a trait or phenotype with a probability greater than expected from random chance (0.5). For example and without limitation, the probability that the one or more markers are passed together may be at least about 0.7; at least about 0.75; at least about 0.8; at least about 0.85; at least about 0.9; at least about 0.91; at least about 0.92; at least about 0.93; at least about 0.94; at least about 0.95; at least about 0.96; at least about 0.97; at least about 0.98; at least about 0.99; and/or essentially 1. While a marker may be comprised in some examples within a gene that determines a particular trait or phenotype, it will be understood that most often a marker may be separated by a short distance from such a gene on the same chromosome. Moreover, it will be understood that most traits or phenotypes are complex (i.e., polygenic), and thus a marker that is linked to a trait or phenotype may in some examples reside within, or be linked to, a QTL underlying a polygenic trait.

The term "linkage disequilibrium" (LD) refers to alleles or loci that associate at a frequency higher than expected for independent alleles or markers, such that they appear as a haplotype. For example, when variants of two genetic loci are in strong linkage disequilibrium, the variant at one locus is predictive of the variant at the other locus on an individual chromosome.

Marker-assisted breeding: As used herein, the term "marker-assisted breeding" may refer to an approach to breeding directly for one or more trait(s) (e.g., a polygenic trait). Marker-assisted breeding provides a time- and cost-efficient process for improvement of plant varieties. Several examples of the application of marker-assisted breeding involve the use of isozyme markers. See, e.g., Tanksley and Orton, eds. (1983) *Isozymes in Plant Breeding and Genetics*, Amsterdam: Elsevier.

In current practice, plant breeders attempt to identify easily detectable traits, such as flower color, seed coat appearance, or isozyme variants, that are linked to an agronomically desired trait. The plant breeders then follow the agronomic trait in the segregating, breeding populations by following the segregation of the easily detectable trait. However, there are very few of these linkage relationships between traits of interest and easily detectable traits available for use in plant breeding. In some embodiments of the invention, marker-assisted breeding comprises identifying one or more genetic markers (e.g., SNP markers) that is/are linked to a desirable trait and may be expressed in terms of HV, and following the desirable trait in a segregating, breeding population by segregation of the one or more genetic markers, for example, to produce particular CHVs/ OHV in a cross. In some examples, the segregation of the one or more genetic markers may be determined utilizing a probe for the one or more genetic markers by assaying a genetic sample from a progeny plant for the presence of the one or more genetic markers.

Single-nucleotide polymorphism (SNP): As used herein, the term "single-nucleotide polymorphism" refers to a DNA sequence variation occurring when a single nucleotide in the genome (or other shared sequence) differs between members of a species or paired chromosomes in an individual. Within a population, SNPs can be assigned a minor allele frequency the lowest allele frequency at a locus that is observed in a particular population. This is simply the lesser of the two allele frequencies for single-nucleotide polymorphisms.

Single nucleotide polymorphisms may fall within coding sequences of genes, non-coding regions of genes, or in the intergenic regions between genes. SNPs within a coding sequence will not necessarily change the amino acid sequence of the protein that is produced, due to degeneracy of the genetic code. An SNP in which both forms lead to the same polypeptide sequence is termed "synonymous" (sometimes called a silent mutation). If a different polypeptide sequence is produced, they are termed "non-synonymous." A non-synonymous change may either be missense or nonsense, where a missense change results in a different amino acid and a nonsense change results in a premature stop codon. SNPs that are not in protein-coding regions may still have consequences for gene splicing, transcription factor binding, or the sequence of non-coding RNA. SNPs are usually biallelic and thus easily assayed. Sachidanandam (2001) Nature 409:928-33.

Infer: As used herein with respect to a genotype, haplotype, QTL, marker, or other genetic element, the term "infer" refers to the deduction of an allelic form from available information. Missing information such as a missing allelic form with respect to any one or more markers (e.g., at a specific locus or genome segment) in the genome of an individual may be inferred. For example, a missing genotype for an ancestor may be inferred using genotype data of an individual in a population related by pedigree to the ancestor. Furthermore, a missing genotype for an individual of a population may be inferred using genotype data of an ancestor related by pedigree to that individual, for example, by employing one or more statistical means.

Selection: As used herein, the term "selection" (or select or selected) refers to one or more systems, processes, steps, or combinations of steps that determine one or more individuals in a population that are to contribute to the next generation (or define a breeding endpoint), including natural selection and artificial selection. In some embodiments, the OHV is determined for possible crosses of each plant in a population with a donor plant. The plant that yields the highest OHV for the cross is then actually crossed with the donor plant, while the other plants in the population may be disregarded or discarded, thereby selecting the plant with the potential to yield the highest OHV for the cross.

Selection "criterion" refers to a characteristic forming the basis for a selection decision, including, for example and without limitation: OHV; the presence or absence of one or more genes; and one or more genetic markers associated with a particular gene, combination of genes, HV, trait, and combination of traits or HVs. Selection index refers to a ranking of selection criteria according to their estimated breeding value. Selection intensity refers to the extent, expressed statistically, to which a breeder adheres to a decision on the selection of a particular individual for breeding. Statistically, the selection intensity may be expressed as the difference between mean selection criterion of those individuals selected to contribute to the next generation and the mean selection criterion of all potential parents, expressed in standard deviation units.

Trait or phenotype: The terms "trait" and "phenotype" are used interchangeably herein. For the purposes of the present disclosure, desirable traits of particular interest include agronomically important traits, as may be expressed, for example, in a crop plant. A desirable trait may be linked to one or more alleles and/or a QTL. In some examples, a desirable trait is the presence of a particular allele (e.g., a GM event). In some examples, a desirable trait is a trait for which HVs have been determined for a plurality of genome segments in a breeding population. In some examples, a desirable trait is a complex or epistatic trait.

Ideotype: The term "ideotype," as used herein, refers to an idealized individual having desired traits or a desired combination of traits. In a breeding program, selective breeding may be carried out with the goal of producing progeny that approach the standard of an ideotype, progeny that more closely resemble the ideotype than inbred parent varieties, and/or progeny that may be used to produce the ideotype via breeding with a further parent variety.

IV. Identifying the (Optimal) Haploid Value

Embodiments herein utilize a determinable value that is specific to each segregating individual (e.g., a breeding cross between two dissimilar or inbred individuals). This value is referred to as the optimal haploid value (OHV). The haploid value (HV) reflects the breeding value (e.g., for at least one trait of interest) of a particular haploid genomic segment. In embodiments, the combined haploid value (CHV) in a haploid individual is a function of HVs in the haploid individual. In particular embodiments, the CHV is the sum of the HVs in the haploid individual. The OHV reflects the highest HV obtainable from a specific individual; for example, the optimal haplotype that can be found in an individual generated from a particular cross. By producing a doubled haploid from a haploid individual identified to comprise the OHV (or a CHV that approaches the OHV), an optimal (or closer to optimal) diploid individual can be created.

The HV is a value that is determinable for a haplotype or multiple segments (for example, as may be defined in cM) of the haplotype. In a particular example, an individual is considered to carry two haplotypes, measuring its entire genome. In some examples, an individual is considered to carry a number of haplotypes, each corresponding to a chromosome in the genome, due to the independent segregation of chromosomes. However, further reductions in haplotype length may allow for additional optimization of selection decisions. Thus, in some embodiments, the genome of the individual is partitioned into segments, each of which is considered a haplotype that has a particular HV. For example, the segments may be defined to have the length that results in the most genetic gain (e.g., whole chromosome or subsets of chromosome, including but not limited to chromosome segments of 100 cM; 95 cM; 90 cM; 85 cM; 80 cM; 75 cM; 70 cM; 65 cM; 60 cM; 55 cM; 50 cM; 45 cM; 40 cM; 35 cM; 30 cM; 25 cM; 20 cM; 15 cM; and 10 cM). In some embodiments, haplotype segments are defined in terms of physical length (e.g., kilobases, and discrete fragments generated by restriction digestion)

The ploidy level of an individual determines the number of haplotypes it carries at any given position/segment. In some embodiments, the individual is diploid. In some embodiments, the individual is polyploid (e.g., triploid, tetraploid, etc.). The extension of OHV calculations for diploid examples provided herein to such polyploid individuals is straight-forward, and can be performed by one of skill in the art without undue experimentation.

Extensions of the OHV concept to polyploidy are simplest if sub-genomic SNP are identified that can be treated as de facto diploid. In particular embodiments, where auto-tetraploid species where sub-genome specific SNP do not exist, adaption of OHV may require the number of potential haplotypes that are passed from parent to offspring to increase. For example, in an auto-hexaploid it would be three. Furthermore, phasing of haplotypes for outbred allo- and auto-polyploids may be desirable in some examples. In particular examples, haplotypes may be tracked through the generations starting from the inbred base population.

A conventional approach for the production of a desirable doubled haploid plant is to select better doubled haploids using genomic selection (GS). Meuwissen et al. (2001), supra. Embodiments herein instead utilize OHV selection to genomically select parent lines and/or progeny thereof to create elite cultivars. OHV and GS are greatly distinguished by the methods used in each selection system to calculate the breeding value on which to select. In GS, the genomic estimated breeding value (GEBV) is calculated as:

GEBV=$F(x,\beta)$, where for a number of loci (Nloci), x is a vector containing indicator variables for the individual's genotype at loci (1:Nloci) (e.g., taking values of 0, 1, or 2), and $\beta$ is the vector of marker allele effects for the loci (1:Nloci). In most cases, $F(x,\beta)$ corresponds to the linear function:

GEBV=$x\cdot\beta$ where · is the dot product operator.

In a typical example of GS, the GEBV is calculated as:

$$GEBV = \sum^{Nloci} x_i \beta_i$$

where $x_i$ is the individual's genotype at locus i (e.g., taking values of 0, 1, or 2), and $\beta$ is the marker allele effect at locus i. Cole and VanRaden (2011), supra, at 447.

In embodiments herein, HVs are employed as the breeding value (instead of GEBV) for selection purposes. A generalized HV is calculated for both haplotypes in a segment as:

HV$_i$=$F(h,\beta_h)$, where h is a vector containing indicator variables for the individual's haplotype at loci (1:SegL), where SegL is the number of loci within a segment and all possible interactions between haplotype loci (SegL+1:SegL $2^{segL}$; assuming only 2 haplotypes at each segment) and across haplotype segments (Nseg+1:Nseg+$2^{Nseg}$), where Nseg is the number of genomic segments; and where $\beta_h$ is a vector of haplotype and haplotype interaction effects corresponding to the indicator variables.

For hybrid crops, a generalized HV can be calculated for each potential tester t given historical hybrid performance as:

HV$_{it}$=$F(h,\beta_{ht})$, where $\beta_{ht}$ is a vector of haplotype and haplotype interaction effects for a given tester t. In cases where interaction effects do not contribute significantly to predictive performance (i.e., no epistasis), the corresponding effects $\beta_h$ or $\beta_{ht}$ are set to zero.

To determine OHV, a generalized calculation can be done that maximizes across all possible haplotype combinations:

OHV=max(HV), where HV is a vector containing all possible HV$_i$ or HV$_{it}$. In examples, multiplying this OHV by 2 allows comparisons with GEBV and corresponds to the full breeding potential of a doubled haploid selected using OHV. As discussed above, the breeding value of progeny selected by OHV is always equal or greater than that selected using GEBV.

In some embodiments herein, HVs are utilized for selection purposes, where HVs are determined for both haplotypes in a segment, for example, according to the function:

$$HV = \sum^{Nloci} h_j \beta_j$$

where j is the locus within the segment, and $h_j$ is the individual's haplotype at locus j. The CHV may be determined for an individual by summing the HVs determined in the individual:

$$CHV = \sum^{Nseg} HV_k$$

where Nseg is the number of genomic segments, and k is the genomic segment. In examples, the best (optimal) HV is determined in each segment, and they are summed over segments to yield the OHV:

$$OHV = \sum^{Nseg} \max(HV_k)$$

In some embodiments, the individual with the highest OHV is not the plant with the highest average genomic breeding value. Thus, the use of OHV results in the selection of a different individual than conventional GS-based methods. As will be appreciated by one of skill in the art after consideration of the foregoing, the OHV of an individual is always equal or greater than its GEBV. Selection by OHV is flexible, and it may be substituted in any method where GS was previously employed. For example, OHV may be combined with introgression in a breeding program and provide benefits over GS in such a breeding program, without incurring any additional cost.

V. Combining OHV and Epistasis

Epistasis (the interaction between one or more loci) may contribute to performance of crops such as wheat. Holland (2001) "Epistasis and Plant Breeding," In *Plant Breeding Reviews*, John Wiley & Sons, Inc., pp. 27-92; Wang et al. (2012) Heredity 109:313-9. However, the evaluation of epistatic interactions is currently highly impractical when all possible pairwise combinations of single nucleotide polymorphisms are considered. For example, given the approximately 90,000 SNPs currently utilized in wheat breeding, testing each interaction would involve the estimation of 4 billion epistatic effects; raising significant issues with regard to statistical power and computational resources.

Known methods of estimating interaction effects include sequential estimation of individual interactions and Bayesian genomic selection methods that simultaneously estimate all effects. De los Campos et al. (2013) Genetics 193:327-45; Erbe et al. (2012) J. Dairy Sci. 95:4114-29; Habier et al. (2011) BMC Bioinform. 12:186; Meuwissen et al. (2001) Genetics 157:1819-29. In sequential estimation, interactions are estimated one at a time. This method, like a genome-wide association study (GWAS), is expected to be suboptimal and is not considered suitable to predict genomic breeding values. Sequential estimation can overestimate allele effects and can suffer from significant multiple-testing problems.

Bayesian genomic selection methods are linear regression models that apply a variety of prior covariates on the distribution of marker effects. This allows Bayesian selection methods to more efficiently accommodate genetic architectures in which some loci have large effects (i.e., by reducing the amount of shrinkage applied to the effects of such loci), as compared to ridge regression methods which shrink all loci effect equally. A particular model for Bayesian genomic selection methods with epistasis is:

$$y = \mu + \Sigma_{q=1}^{l} \gamma_q x_{iq} a_q + \Sigma_{q1 < q2}^{l} \gamma_{q1q2} x_{iq1} x_{iq2} b_{q1q2} + e,$$

where l is the number of loci, $y_i$ is the phenotype of individual i, $\mu$ is the mean, $\gamma$ is an indicator variable designating whether the locus or interaction has an effect, $x_{iq}$ is the genotype of individual i at locus q, $a_q$ is the additive effect of locus q, $b_{q1q2}$ is the interaction effect of locus q1 and q2, and e is the residual. Yi et al. (2003) Genetics 165:867-83.

Table 1 is illustrative of an interaction space that may be explored using methods according to some embodiments herein. For example, genotype by genotype interaction effects may be estimated per pair of loci, where A is locus 1 and B is locus 2. Aa is assumed to be the same as aA for simplicity in this illustration.

TABLE 1

Exemplary interaction space.

|  | BB | Bb | bb |
|---|---|---|---|
| AA | <u>AABB</u> | AABb | <u>AAbb</u> |
| Aa | AaBB | AaBb | Aabb |
| aa | <u>aaBB</u> | aaBb | <u>aabb</u> |

Genotype interactions relevant to doubled haploids are underlined.

In some embodiments herein, a method estimates interaction effects in a breeding program that uses only double haploids. Because heterozygous genotypes do not occur in doubled haploids, there is no need to estimate their interaction effects. Thus, the number of interaction effects per loci pair illustrated in Table 1 is reduced from 9 to 4.

Advantages of particular methods herein provide the significant benefit of reducing the complexity of epistatic interactions in a selection program. For example, in wheat there are approximately 90,000 SNP markers currently being used for breeding selection. In a breeding program evaluating homozygotes and heterozygotes for all 90,000 markers, there are 90,000*(89999/2)*9=36.4 billion potential interactions. The number of interactions is reduced significantly (by more than 20 billion) in a method herein utilizing OHV selection of doubled haploids, in which there are, for the same example, 90,000*(89999/2)*4=16.2 billion interactions.

Some Embodiments herein may be used to further reduce the number of interactions that need to be to be calculated. In particular embodiments, epistatic effects are calculated within a haplotype only, and subsequently added to the OHV value to produce an "OHVe" value for an individual that is a function (e.g., the sum) of epistatic effects within the haplotype and OHV. Furthermore, potential interactions across entire OHV segments may be calculated in certain embodiments to account for interactions at greater genomic distances. For example, the value for an individual haplotype with epistasis within an OHV segment can be calculated as:

$$HVe = \Sigma_{k=1}^{m} h_k \beta_k + 0.5 \Sigma_{q=1}^{p} hh_q \varepsilon_q,$$

where m is the number of loci with an OHV segments, p is the number of interactions within an OHV segment (for example, calculated as $$m\left(\frac{m-1}{2}\right)),$$

$hh_q$ is the $q^{th}$ genotype by genotype interaction (e.g., which can take the form AABB, AAbb, aaBB, or aabb), and $\varepsilon_q$ is the epistatic effect at the $q^{th}$ interaction. Thus, in some examples, the OHVe may be calculated as:

$$OHVe = 2\sum_{o=1}^{n} \max(HVe_o)$$

In certain embodiments, the epistatic effects calculated across different OHV segments are prioritized to the most common haplotypes. For example, OHVe that includes epistatic effects across different OHV segments may be calculated as:

$$OHVe = 2 \Sigma_{o=1}^{n} \max(HVe_o + \Sigma_{s=1}^{r} H_s \delta_s),$$

where n is the number of OHV segments, r is the total number of interactions across segments and depends on the number of OHV segments m, $H_s$ is the $s^{th}$ common haplotype by common haplotype interaction, $\delta_s$ is the epistatic effect for the $s^{th}$ interaction. To illustrate, if number of common haplotypes is assumed to be 10, r can be calculated as (n*10)((n*10−1)/2). It is possible in some examples that the sum of the epistatic interactions across segments will be greater than the HVe within a segment.

VI. Methods for Plant OHV Selection

Some embodiments herein provide methods for plant selection that may be used, for example, to facilitate the production of new, desirable plant lines. Embodiments herein include methods that may be employed to select any suitable plant (or tissue thereof) that is capable of generating a doubled haploid. Suitable plants also include those suitable for self-crossing or "selfing," which differs from outcrossing. Suitable plants that are capable of generating a doubled haploid and/or selfing include, for example and without limitation: alfalfa, apple, banana, bean, broccoli, castorbean, citrus, clover, coconut, coffee, cucumber, Douglas fir, *Eucalyptus*, Loblolly pine, linseed, melon, oat, olive, palm, pea, peanut, pepper, poplar, *Radiata* pine, sorghum, Southern pine, strawberry, sugarbeet, sugarcane, sunflower, sweetgum, tea, tobacco, tomato, turf, *Arabidopsis thaliana*, barley, maize, cotton, rapeseed/canola, rice, rye, soybean, and wheat. In particular embodiments, the disclosed methods can be used to determine HV, CHV, and/or OHV for the production of doubled haploids of barley, maize, cotton, rapeseed/canola, rice, rye, soybean, and/or wheat. A tissue suitable for generating a double haploid plant may be, for example and without limitation, a seed, embryo, or embryogenic tissue (e.g., embryogenic callus, anther, or microspore cultures).

Methods according to particular embodiments may offer any of several advantages over plant selection methods as they are currently practiced, such as, for example, phenotypic selection and/or genomic selection. In some examples, an OHV selection method provides, for example and without limitation, a cost and resource savings to the plant breeder, and increased genetic gain and/or genetic diversity over several generations of plant development.

In some embodiments, the method comprises determining the genomic CHV for an individual haploid plant/tissue (or doubled haploid thereof), such as may be produced from a progeny plant resulting from the cross of a first parent plant and a second parent plant, comparing the CHV of the plant with the OHV determined for the progeny plant, and selecting the haploid plant/tissue, (or doubled haploid thereof) if the CHV approaches the OHV. In particular embodiments, a doubled haploid plant is produced from a selected haploid plant/tissue. The doubled haploid plant may then be cultivated as a new elite line, or may be utilized in further steps of plant breeding.

In examples, a CHV approaches the OHV when the CHV is identical to the OHV, the CHV is substantially identical to the OHV, the CHV is the closest to the OHV of all the CHVs determined in a progeny population, and/or the CHV is close enough to the OHV that the skilled artisan decides that closer identity is not required. A CHV may approach the OHV if, for example, the CHV is at least 100%, 99%, 98%, 96%, 95%, 94% 93%, 92%, 91%, 90%, 89%, 88%, 87%, 86%, 85%, 84%, 83%, 82%, 81%, and/or 80% of the OHV. In some examples, a plurality of haploids from a segregating plant are analyzed to determine their highest CHV, and the CHV of the selected haploid is closer to the OHV of the segregating plant than the CHV of a specific percentage (e.g., 99%, 98%, 96%, 95%, 94% 93%, 92%, 91%, 90%, 89%, 88%, 87%, 86%, 85%, 84%, 83%, 82%, 81%, or 80%) of the other haploids analyzed.

HVs may be determined for a haploid or doubled haploid individual or tissue thereof, for example, by genotyping the individual or tissue (e.g., using a kit provided in systems herein), and identifying markers that are linked to breeding values of one or more genomic segments for a trait of interest. When summed, such HVs yield the CHV of individual haploid or haploid tissue. In particular embodiments, a genomic OHV is also determined for a segregating individual (e.g., by reference to its parent plant genotypes), and a haploid produced from the individual is selected to produce an elite doubled haploid plant if its CHV equals or approaches the OHV.

Some embodiments provide methods for evaluating the potential of a line cross to produce an elite double haploid (possibly containing a desirable allele or GM event), which then may be selected for further breeding. For example, the highest possible OHV may be determined for progeny produced from a theoretical cross between a first plant candidate and one or more second plants. If the determined highest possible OHV for progeny produced in a theoretical cross the first plant satisfies a pre-determined criterion, then the first and second plant(s) are crossed to produce $F_1$ progeny. In some examples, the criterion is the condition that a first plant candidate can produce a progeny having the highest possible OHV among a progeny that can be produced from a plurality of plant candidates for the theoretical cross. For example, the OHVs may be determined for progeny of a theoretical cross between a transgenic plant and each of a plurality of candidate plants, and the transgenic plant may be crossed with the plant of the plurality that yields a progeny having the highest OHV (from among those producible in crosses from each of the plurality of plants) in the theoretical cross with the first plant.

In particular embodiments, a method is provided that comprises determining the OHV for progeny of a first and at least a second plant, producing a population of haploids from the progeny plants, selecting at least one of the haploids for a CHV that approaches the OHV determined for the progeny, and producing a doubled haploid from each of the selected progeny plant(s). In particular embodiments, the first plant comprises an allele or transgenic event that is introgressed into the elite doubled haploid plant.

In some embodiments herein, OHV selection is incorporated in a breeding process using in vivo haploid induction. Such a process may comprise steps including, for example and without limitation: intercrossing selected lines, creating new genetic variation; in vivo haploid induction in generation $F_1$ (or in a subsequent generation such as $F_2$, $F_3$, or later); chromosome doubling of haploid seedlings; producing doubled haploid progeny; transplanting and selfing of doubled haploid plants (generation Do); evaluation of Di lines (e.g., in single-row observation plots) and optionally and in parallel, multiplication by selfing; evaluation of test crosses (e.g., in multi-environment trials); and build-up of experimental hybrids.

The expected gain from selection can be described by the formula:

$$\Delta G = i \, hx \rho G \sigma y,$$

where i is the selection intensity; hx is the square root of the heritability of the selection criterion; ρG is the genetic correlation between selection criterion and gain criterion; and σy is the standard deviation of the gain criterion. In long-term breeding programs, the gain criterion typically used for evaluating selection progress is the general combining ability (GCA) of the improved lines. Test units are, at the beginning of a breeding cycle, the doubled haploid lines per se. Later in the cycle, the test units are test-crosses.

Strong selection (large i) is expected to lead to a small effective population size, and consequently to a loss of genetic variance due to random drift. To keep this loss within certain limits, a minimum number of lines has to be recombined after each breeding cycle. This number depends on the inbreeding coefficient (F) of the candidate lines. It is generally understood that the value of F should be 2 times larger for inbred lines than for non-inbred genotypes. Assuming that $S_2$ lines (F=0.75) are recombined in conventional breeding, the number of doubled haploid lines (F=1) would therefore be increased 1:0.75=1.33 fold to preserve an equivalent level of genetic variation. Thus, selection intensity may be reduced accordingly when using doubled haploid lines.

In contrast to the selection intensity, hx and ρG are typically increased when using doubled haploid lines, particularly in the first testcross stage. Neglecting epistasis, in inbred lines:

$$\Delta GCA = \tfrac{1}{2} F \sigma 2A,$$

where σ2A is the additive variance of the base population. Thus, the GCA variance of doubled haploid lines is 1:0.75=1.33 times larger than that of $S_2$ lines. This leads to a better differentiation among the test-crosses, and consequently to a higher heritability. For example, when three sets of $S_2$ and $S_3$ lines are each compared with doubled haploid lines derived from the same crosses, and evaluated with the same testers in the same environments, the estimated genetic testcross variances for grain yield amounted to an average of 50 bu/acre ($S_2$), 94 bu/acre ($S_3$), and 124 bu/acre (DH).

The genetic correlation between selection and gain criterion (ρG) also increases according to the degree to which the tested lines are inbred. For example, the correlation between St lines and their homozygous progenies for GCA is equal to √Ft, whereas for doubled haploid lines the correlation is 1. Thus, compared with $S_2$ lines, the correlation of doubled haploid lines is 1:√0.75=1.15 times stronger.

The genetic standard deviation of the gain criterion (σy) is a population parameter and therefore depends on the base population (i.e. not on the breeding procedure).

Embodiments herein may include genotyping a plant, wherein the genotype of a haploid or doubled haploid plant is also the haplotype of the individual. Genotyping may comprise detecting one or more markers (e.g., SNPs) in a sample from an individual, and analyzing the results obtained to determine the allelic form of the subject. In some examples, a sample from the individual comprises nucleic acid (e.g., RNA and genomic DNA). For example, a plant may be genotyped by testing a sample from any part of the plant (e.g., leaf, floral organ, and seed). The sample may be prepared on a solid matrix for histological analyses, or in a suitable solution, such as, for example and without limitation, an extraction buffer or suspension buffer.

A breeding program that incorporates OHV selection may comprise randomly mating of parents. In some embodiments, however, a program is designed that seeks to combine parents with strengths in different genome segments through OHV selection, so as to increase the probability of offspring carrying all strong genomic segments. For example, the haplotype composition of an ideal plant may be generated in silico, and a breeding program may be devised to attain it by using OHV selection to select one or more lines from an available library. Such breeding programs provide accelerated breeding of plants with strengths in specific desirable traits.

In some embodiments herein, the benefits obtainable through OHV selection are expressed in relation to results obtained using marker-assisted EBV (MEBV) selection. MEBV may be calculated from genome-wide DNA markers by a process consisting of three steps: using the markers to deduce the genotype of each individual at each QTL; estimating the effect of each QTL genotype on the trait of interest; and summing the QTL effects for selection candidates to obtain their genomic EBV (MEBV).

The simplest method to deduce QTL genotypes is to identify the markers as QTLs, and to estimate the effects of the marker alleles on the trait of interest. The proportion of the QTL variance explained by the markers ($r^2$) is dependent on the LD between the QTL and the marker or a linear combination of markers. The average $r^2$ declines as the distance between the marker and the QTL increases. An alternative to using single marker genotypes is to construct haplotypes based on several markers. A QTL that is not in complete LD with any individual marker may be in complete LD with a multi-marker haplotype. The advantage of haplotypes over single markers decreases as the $r^2$ between adjacent markers increases.

A least squares method may be employed to estimate the MEBV of each QTL on a trait. Least squares estimates correspond to assuming a prior distribution of QTL effects with an infinitely large variance. Using least squares, only a QTL with large effect will be detected and used. Thus, not all of the genetic variance will be captured by the markers. By assuming that the QTL effects are drawn from normal distribution with constant variance across chromosome segments, a BLUP estimate may be derived, wherein all the effects are estimated simultaneously. Any method that estimates marker effects can be used, for example, ridge regression BLUP, BayesA, BayesCπ, or BayesR (See Erbe et al. (2012) J. Dairy Sci. 95:4114-29; Habier et al. (2011) BMC Bioinformatics 12:186; Meuwissen et al. (2001), supra), because the estimation step of the marker effects is identical in genomic selection and OHV selection.

The extent of recombination may be a major factor influencing the advantage of OHV over GS. The creation of elite doubled haploids requires that good haplotypes are combined in one individual. The accumulation of recombination, either through crossing or doubled haploidy, increases the number of different haplotype combinations, the best of which can then be selected using genomic tools. There are considerable costs involved in forcibly outbreeding a natural inbreeder, such as wheat. However, these costs may be offset by increased genetic gain through the use of OHV, and by selecting for multiple traits simultaneously via a multiple trait selection index approach. The second component will drastically reduce the time spent in backcross and trait stacking cycles.

Relying on naturally occurring recombination may be limiting factor in areas of the genome that tend not to recombine. There is some evidence that areas of low recombination exist in wheat, for example, near the Sr36 introgression (Cavanagh et al. (2013) Proc. Natl. Acad. Sci. USA 110(20):8057-62), or near telomeres. In contrast, distal ends on chromosomes exhibit higher recombination rates. Akhunov et al. (2003) Genome Res. 13:753-63. These recombination differences are expected to affect each method equally. However, extension of OHV methodology with dynamic haplotype lengths to account for differential recombination rates may further increase its performance.

The end goal in plant breeding is typically a superior fixed line, and this is currently accomplished in large part with doubled haploids. A line is "fixed" only if it has potential to produce elite germplasm. OHV selects explicitly on the potential genetic value of such a line. OHV selection more closely matches this ultimate goal and, thus, performs better than GS. OHV is finely tuned to what is achievable in one cycle of recombination (i.e. doubled haploidy). The superiority of the performance of OHV may be reduced when haplotype lengths considered in the OHV steps are reduced substantially, and the plant's potential is evaluated too far into the future.

OHV selection may be carried out in any inbred or outbred species. Its advantages may be most clear when doubled haploids are produced, and when the genetics in production environments are separate but derived from a breeding population. The increased genetic diversity possible by OHV selection means that, overall, the GEBV of the breeding population will be slightly lower than with conventional GS. However, the ability of OHV selection to produce elite doubled haploids is increased. This may be particularly advantageous in a system where elite varieties are commercialized to growers, such as most plant breeding programs. The utility of OHV selection does not simply follow from, or carry over to, other breeding programs (e.g., dairy cows), because it is not clear in those systems that the increase in long-term genetic gain is worth the short-term reduction in uniformity due to increased genetic variance.

VII. System for Plant OHV Selection

Some embodiments herein include plant selection systems comprising a kit for determining the genotype(s) of one or more plants; a database; means for determining a OHV from the genotype(s); and a user interface allowing a user to input haplotype information, wherein the system determines an OHV for the one or more plants. In particular embodiments the kit is used to genotype a half seed or very young plant (e.g., a haploid plant or doubled haploid plant). In some examples, the means for determining a OHV from the genotype(s) is analytical programming. In some examples, the means for determining a OHV from the genotype(s) is a reference chart.

Particular embodiments provide a high-throughput plant OHV selection system comprising a kit for determining the genotype(s) of one or more plants, wherein the kit comprises a solid support having polynucleotides bound thereto, wherein each polynucleotide hybridizes to a polymorphic genetic marker that is linked (e.g., tightly-linked, and very tightly-linked) to a genome segment haplotype that is associated with a breeding value for a trait of interest. In some examples, the kit comprises a hybridization medium (e.g., a microfluidic device or homogenous assay medium). Exemplary microfluidic devices include those having solid supports with micro-channels. See, e.g., U.S. Pat. Nos. 5,304,487; 5,110,745; 5,681,484; and 5,593,838. In some examples, the kit comprises a "chip" having bound to the surface thereof, for example and without limitation, about 10,000-100,000 oligonucleotides, each of which consists of a sequence that specifically hybridizes to a particular SNP.

Polynucleotides bound to a solid support of certain embodiments herein are oligonucleotides that are attached directly or indirectly to the solid support. The oligonucleotides may be used to determine HVs in an individual from which a nucleic acid sample has been obtained, by the determining the occurrence of a marker that is linked to the HV, by virtue of the specific hybridization of nucleic acid from the individual to an oligonucleotide bound to the solid support. In some examples, a plurality of polynucleotides is immobilized onto discrete regions of the solid substrate, wherein binding of nucleic acid from the sample to a particular region of the substrate is determinative of the presence of the marker in the sample.

High-throughput systems of certain embodiments herein may include, for example and without limitation, a platform such as the UHT SNP-IT platform (Orchid Biosciences, Princeton, N.J., USA); MASSARRAY® system (Sequenom, San Diego, Calif., USA); and the integrated SNP genotyping system (Illumina, San Diego, Calif., USA).

Particular embodiments include a kit for determining the haplotype(s) of one or more plants via a PCR-based assay (e.g., TTAQMAN® PCR-based assays (ABI, Foster City, Calif., USA)). Such embodiments in some examples may include an automated, fully-automated, or manual (e.g., bench-top) assay procedure and equipment.

VIII. Combining Introgression and OHV Selection

Introgression is the incorporation of a plant line's desirable characteristic(s) into a plant that does not comprise the desirable characteristic(s). The characteristic to be introgressed in some examples is a single allele, for example, a genetic modification event. In some embodiments herein, a method and/or system for OHV selection is utilized to facilitate the introgression of an allele of interest (e.g., a GM event) into a recurrent parent plant that has mostly favorable characteristics. In particular embodiments, the introgression is performed within the context of a breeding program that seeks to produce plants comprising a desirable level of expression of the trait of interest, which trait of interest may be used as the trait for which HV breeding values are determined and employed in OHV selection.

New traits or genes are typically introgressed from a donor line to a recurrent line via crossing. In this process, an $F_1$ generation is created, and then is backcrossed to the recurrent line to regain the original background, while retaining the new trait/allele. See, e.g., Tanksley (1983) Plant Mol. Biol. Rep. 1(1):3-8; Visscher et al. (1996) Genetics 144:1923-32; Hospital (2001) Genetics 158:1969-79. When the donor line is inferior for traits other than the trait that is the target of the introgression, the recurrent line's background is typically desired. Generally, the utility of such a backcrossing strategy depends upon identifying progeny with markers from the recurrent parent that are as close as possible to the introgressed target locus.

OHV selection methods and/or systems herein exploit specific features of plant breeding that can accelerate the rate of genetic gain and/or improve the maximum genetic gain. Embodiments herein improve the utility of backcrossing by identifying progeny that comprise desirable haplotype genome segments from both parents, regardless of whether the average breeding value of, for example, the donor parent is less than the recurrent parent. Traditional introgression that recovers the original background will only ever achieve the original genetic level of the elite line. The great advantage of OHV introgression is that populations can be selected on while introgression occurs. This will allow for increased genetic gain in plant breeding programs and will lead to elite lines with introgression events that are superior to the original elite background.

Embodiments herein that incorporate OHV selection into an introgression process may reduce the time necessary to arrive at an ideotype. In some embodiments, a plant comprising an allele of interest is crossed with a second plant comprising mostly favorable characteristics. Haploid values (HV) for the trait may be determined for each haploid genome segment in the first and second plant. Using this determination, the OHV may then be determined as the best doubled haploid that could be produced from progeny of the cross.

In particular embodiments, doubled haploids are created from progeny of the cross until an individual having the allele of interest and the OHV, or a CHV very close to the OHV, is created. In some examples, the doubled haploid comprising the allele of interest and the CHV that comes closest to the OHV is selected for utilization in further steps of the breeding program. For example, the selected doubled haploid may be backcrossed for one or more additional generations to the recurrent parent plant, wherein OHV selection may be performed at each generation, so as to produce a new variety wherein the allele of interest has been introgressed into the recurrent parent variety in a manner that optimizes genetic gain and genetic diversity in the new variety.

In certain embodiments, an introgression program incorporating OHV selection is used to simultaneously introgress one or more desired alleles from one or several sources selected from the group consisting of, for example and without limitation: wheat lines or grasses; genetic modification (e.g., for delayed plant senescence, and glyphosate tolerance); genome editing; and stacking of transgenes at a locus.

In certain embodiments, an introgression program incorporating OHV selection applies genomic prediction of OHV to inform selection decisions. Selection cycles in such a program may include sources of variation including, for example and without limitation: genomic prediction of OHV (including random GM events and stacking of transgenes at loci); and sequential introgression of desirable alleles in subsequent generations (e.g., including recurrent cycles of double haploid production).

In certain embodiments, an introgression program incorporating OHV selection identifies new selection entry points in plant breeding. For example, new entry points in some examples include, for example and without limitation, the prediction of alloplasmic effects and epistasis, and the interaction of cytoplasms (e.g., mitochondrial-chondriome and chloroplast-plastome) with nuclear haplotypes; for example, leading to the prediction of Optimal Cytoplasmic Values (OCVs), including prediction of effects of mtDNA and chloroplast populations in alloplasmic lines.

Accordingly, in some embodiments, OHV provides for the selection of populations during introgression to improve the genetic background into which the selected trait is introgressed. This particular embodiment differs from traditional introgression, in which repeated crossing with the recurrent (elite) parent background is intended to reestablish the (elite) parent background. By contrast, use of OHV in plant breeding programs can lead to an improved elite line with introgression events and a genetic background that is superior to the original elite background.

In embodiments, OHV selection can be used when a line with multiple desired events (e.g., 2, 3, 4, 5, 6, 7, 8, 9, or 10 desired events) is crossed with an elite line to introgress the multiple desired events into the elite line's genotype. In some embodiments, multiple lines that have desired events are crossed with one or more elite lines to introgress each of the desired events from the multiple lines into the elite background genotype.

The following examples are provided to illustrate certain particular features and/or embodiments. The examples should not be construed to limit the disclosure to the particular features or embodiments exemplified.

EXAMPLES

Example 1: Comparison of GS and OHV Breeding Programs

Plant breeding programs utilizing OHV selection were directly compared to programs utilizing GS. The comparison was performed with a base population of empirically determined genotypes for 4,788 SNPs from 1110 wheat lines (empirical Illumina iSELECT™ Bead Chip 9K array genotypes (Cavanagh et al. (2013), supra), which ensured a realistic linkage disequilibrium structure.

These SNPs were placed on 21 chromosomes, each measuring 150 Morgans (3 genomes and 7 chromosomes each). The genome was then divided into segments of equal lengths of 50 cM, which resulted in approximately 3 segments per chromosome.

During the creation of gametes, either for conventional offspring, or during doubled haploid production, recombinations were randomly placed on the genome at a rate of 1 per Morgan. Allele substitution effects were sampled from a double exponential distribution for 500 loci, reflecting a quantitative trait that is influenced by many causative variants.

Two breeding scenarios were simulated: GS, where selection was based on GEBV, and OHV. GS and OHV selection were then compared on exactly the same breeding program. All parameters, such as selection intensity, were the same between GS and OHV, and the only difference was that selection was either on GEBV or OHV. Instead of estimating marker effects based on linked phenotypes, the true marker effects were used and selection was based on true marker effects.

The generic breeding program was as follows, and specific scenarios are described subsequently. Of the initial inbred 1110 lines, the best 30% were used as parents of the $F_1$ generation to achieve a population size of 55,000 individuals. Every selected inbred line was crossed with all other selected lines. One progeny was then genotyped per cross (as all were identical), and the top individuals were selected to produce the next generation ($F_2$). In the outbred $F_2$ to $F_{10}$ generations, it was assumed that each individual could only be mated to only one other individual due to limited seed. All mating was random. The number of offspring per outbred cross was varied, and the total breeding population was kept constant at 55,000 individuals by varying selection intensity. In each generation, the most elite plants were selected for doubled haploid production, and a varied number of doubled haploids was produced. The most elite doubled haploids could optionally be used for breeding two generations later to account for the time-lag for creation and doubled haploid seed collection. This was then repeated for several generations, and in each generation OHV and GEBV was recalculated, which captured new recombination events.

In the DEFAULT scenario, 100 offspring were produced per outbred cross, 10 elite individuals were selected to create 100 doubled haploids each, and the best 50 doubled haploids were cycled back into the breeding program. Various scenarios investigated the number of: offspring produced per outbred cross (nOff), elite individuals selected to produced doubled haploids (nEliteInd), doubled haploids produced per elite individual (nDH), elite doubled haploids cycled back into the breeding program two generations later (nDH-cycled), QTL simulated (nQTL), haplotype segments per chromosome (nSeg), and the number of generations (nGen).

Example 2: Increased Genetic Gain and Genetic Variation with OHV Selection

Figure 2:
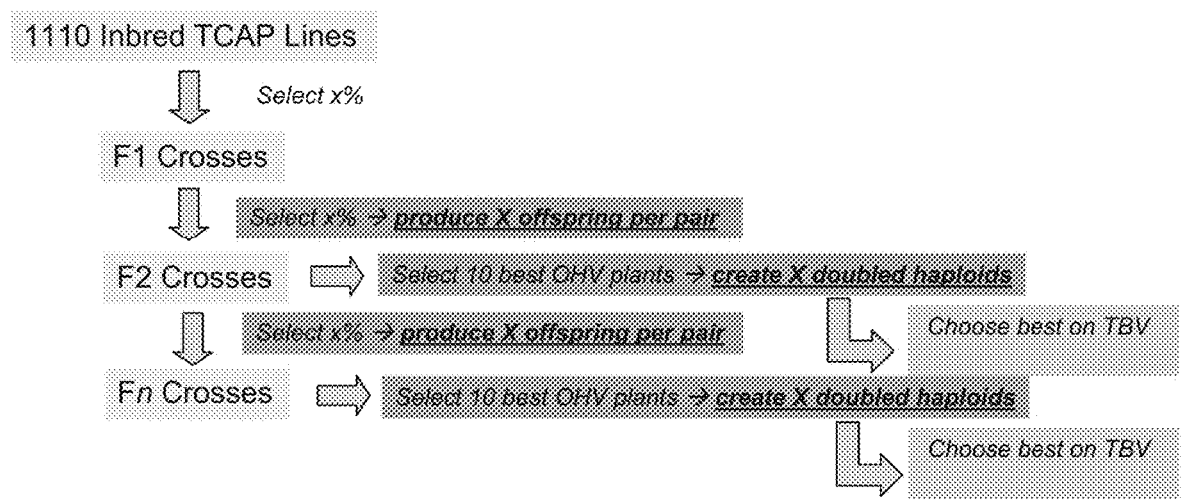
FIG. 2 includes the general structure of an exemplary breeding program utilizing OHV selection, where crosses may be repeated for n generations, and elite fixed lines may be created in each generation.

Certain points in the breeding cycle that have been determined to be important when trying to increase genetic gain are shown in FIG. 2. Relevant considerations include the number of offspring per pair of outbred plants, and the number of doubled haploids produced per elite plant. Several variations of these factors were tested. The number of offspring per pair was varied between 5, 20, 100, 200, and 1000. The number of doubled haploids produced was varied between 200, 500, and 1000. 100 replicates were run for each variation, and within each replicate the marker effects and base population were identical for GS and OHV selection. All scenario groups and levels within are listed in Table 2. Each scenario was replicated 100 times, and standard errors (SE) are given in Tables and Figures. The results on genetic gain focus on the difference between OHV and GS in genetic standard deviations (SD) of the base generation (i.e., gain OHV−gain GS). Genetic diversity is reported as the true genetic variance, calculated as the variance of all GEBVs in a generation.

TABLE 2

Groups investigated.

| Scenario Group | Variation | Levels |
| --- | --- | --- |
| DEFAULT | Default scenario | nOff 100, nEliteInd 10, nDH 100, nDHcycled 50, nQTL 500, nSeg 3, nGen 10 |
| nOff | Number of offspring per outbred cross | 10, 20, 50, 80, 100, 200, 500, 1000 |
| nEliteInd | Number of elite individuals chosen to produce DHs | 1, 5, 10, 20, 50, 100 |
| nDH | Number of DHs produced per elite individual | 10, 20, 50, 80, 100, 200, 500, 1000 |
| nDHcycled | Number of DHs cycled back into breeding program | 0, 10, 20, 50, 80, 100, 200, 500 |
| nQTL | Number of QTL simulated | 100, 500, 1000 |
| nSeg | Number of haplotype segments per chromosome | 1, 2, 3, 6, 12 |
| nGen | Number of generations | 10, 20 |

Level in bold font is the DEFAULT scenario.

In each generation, 50,000 total progeny were created. This had implications on selection intensities in scenarios where different numbers of offspring were produced per breeding pair. When the number of progeny per pair rose, then the number of breeding pairs had to be reduced accordingly to keep the population size constant within a generation.

In each generation, results obtained via GS and OHV selection were compared using the following statistics: genetic variance; mean genetic level of breeding population; best 10 individuals; and best doubled haploid.

Selection based on OHV versus GS was found to increase genetic gain by up to 0.58 genetic SD by generation 10. In our simulated breeding program, recombination occurred in the creation of offspring and doubled haploids. It was found that if we increase the opportunity of recombination, either by increasing the number of offspring or the number of doubled haploids, we can increase the probability that good haplotypes are combined. Both processes increase the number of recombinations in elite germplasm of the breeding population, but OHV selection is better able to capitalize on that.

Figure 3A:
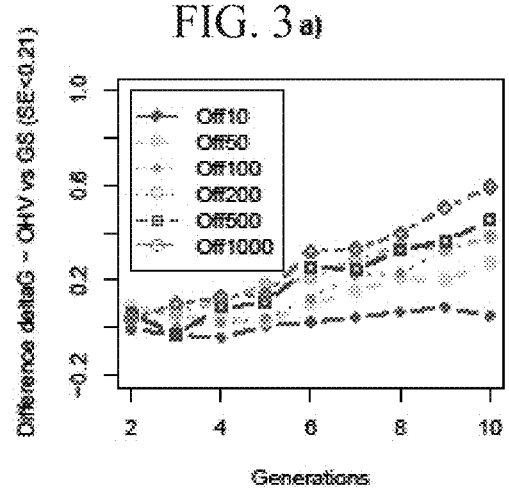
FIGS. 3a-3d includes a graphical representation illustrating advantages of OHV selection over GS, including better genetic gain using OHV instead of GS (genetic base SD from generation 2 to 10). The vertical axis shows the difference in genetic gain (deltaG) between OHV and GS, when varying the number of offspring per outbred cross (nOff) (FIG. 3a); varying the number of doubled haploids produced per elite plant (nDH) (FIG. 3b); the DEFAULT scenario is continued for 20 generations (nGen) (FIG. 3c); and varying the number of elite individuals taken to doubled haploid production (nEliteInd) (FIG. 3d).

There was a clear and increasing advantage in genetic gain of OHV as the number of offspring is increased. FIG. 3a; Table 3.

TABLE 3

Difference in genetic gain between OHV and GV when varying the number of offspring produced per cross (nOff).

| Gen | Off10 | SE Off10 | Off20 | SE Off20 | Off50 | SE Off50 | Off80 | SE Off80 |
| --- | --- | --- | --- | --- | --- | --- | --- | --- |
| 2 | −0.005 | 0.136 | −0.022 | 0.128 | 0.092 | 0.134 | 0.048 | 0.132 |
| 3 | −0.029 | 0.119 | 0.029 | 0.146 | 0.048 | 0.166 | 0.048 | 0.169 |
| 4 | −0.041 | 0.140 | −0.019 | 0.136 | 0.035 | 0.136 | 0.049 | 0.130 |
| 5 | 0.008 | 0.127 | −0.021 | 0.121 | 0.026 | 0.149 | 0.106 | 0.127 |
| 6 | 0.025 | 0.122 | 0.127 | 0.115 | 0.099 | 0.117 | 0.078 | 0.142 |
| 7 | 0.044 | 0.148 | 0.095 | 0.120 | 0.154 | 0.129 | 0.183 | 0.117 |
| 8 | 0.067 | 0.125 | 0.112 | 0.114 | 0.208 | 0.119 | 0.239 | 0.119 |
| 9 | 0.086 | 0.143 | 0.164 | 0.131 | 0.198 | 0.117 | 0.297 | 0.126 |
| 10 | 0.051 | 0.123 | 0.188 | 0.116 | 0.274 | 0.105 | 0.363 | 0.130 |

| Gen | Off100 | SEOff100 | Off200 | SE Off200 | Off500 | SE Off500 | Off1000 | SE Off1000 |
| --- | --- | --- | --- | --- | --- | --- | --- | --- |
| 2 | 0.059 | 0.131 | 0.051 | 0.154 | 0.059 | 0.134 | 0.036 | 0.134 |
| 3 | −0.001 | 0.131 | 0.066 | 0.127 | −0.027 | 0.135 | 0.101 | 0.150 |
| 4 | 0.024 | 0.136 | 0.108 | 0.129 | 0.086 | 0.151 | 0.129 | 0.148 |
| 5 | 0.039 | 0.138 | 0.185 | 0.128 | 0.105 | 0.131 | 0.138 | 0.152 |
| 6 | 0.125 | 0.127 | 0.211 | 0.140 | 0.258 | 0.162 | 0.320 | 0.168 |
| 7 | 0.222 | 0.125 | 0.281 | 0.167 | 0.242 | 0.142 | 0.331 | 0.170 |
| 8 | 0.228 | 0.124 | 0.350 | 0.148 | 0.329 | 0.159 | 0.396 | 0.185 |
| 9 | 0.328 | 0.117 | 0.329 | 0.143 | 0.364 | 0.165 | 0.503 | 0.194 |
| 10 | 0.374 | 0.126 | 0.382 | 0.118 | 0.451 | 0.173 | 0.592 | 0.218 |

Figure 3B:
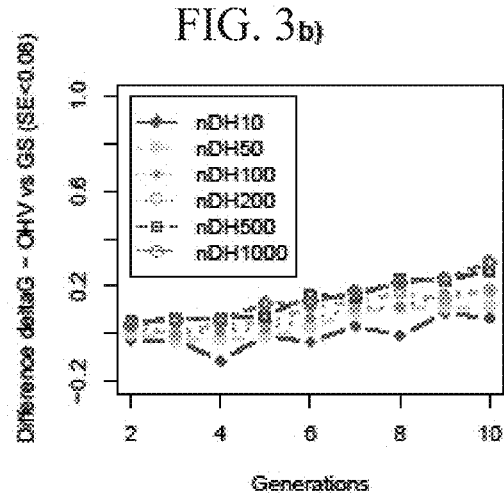

The number of doubled haploids produced from a plant was another factor found to affect genetic gain. As the number of doubled haploids produced from the 10 best individuals was increased, the difference between OHV and GS also increased. FIG. 3b; Table 4. Moreover, OHV selection is better than GS in benefiting from this factor, regardless of the number of doubled haploids produced. The efficiency of achieving the OHV is improved as the number of doubled haploids produced is increased at relatively small numbers (e.g., when less than about 100 doubled haploids are produced per elite plant).

TABLE 4

Difference in genetic gain between OHV and GV when varying the number of doubled haploids produced per elite individual (nDH).

| Gen | DH10 | SE DH10 | DH20 | SE DH20 | DH50 | SE DH50 | DH80 | SE DH80 |
| --- | --- | --- | --- | --- | --- | --- | --- | --- |
| 2 | −0.029 | 0.079 | −0.032 | 0.077 | 0.001 | 0.073 | 0.015 | 0.073 |
| 3 | −0.026 | 0.082 | 0.013 | 0.073 | −0.028 | 0.075 | 0.019 | 0.076 |
| 4 | −0.111 | 0.083 | −0.050 | 0.073 | −0.018 | 0.068 | 0.018 | 0.069 |
| 5 | −0.008 | 0.079 | 0.014 | 0.071 | −0.013 | 0.073 | 0.050 | 0.062 |
| 6 | −0.033 | 0.069 | 0.018 | 0.076 | 0.026 | 0.072 | 0.060 | 0.066 |
| 7 | 0.033 | 0.075 | 0.037 | 0.068 | 0.095 | 0.066 | 0.076 | 0.070 |
| 8 | −0.006 | 0.066 | 0.083 | 0.066 | 0.111 | 0.073 | 0.075 | 0.063 |
| 9 | 0.086 | 0.073 | 0.100 | 0.065 | 0.106 | 0.057 | 0.130 | 0.062 |
| 10 | 0.067 | 0.069 | 0.100 | 0.067 | 0.117 | 0.054 | 0.128 | 0.067 |

| Gen | DH100 | DH100 | DH200 | SE DH200 | DH500 | SE DH500 | DH1000 | SE DH1000 |
| --- | --- | --- | --- | --- | --- | --- | --- | --- |
| 2 | 0.029 | 0.066 | 0.027 | 0.067 | 0.052 | 0.065 | 0.043 | 0.057 |
| 3 | −0.001 | 0.066 | 0.004 | 0.074 | 0.063 | 0.068 | 0.059 | 0.075 |
| 4 | 0.012 | 0.068 | 0.042 | 0.061 | 0.064 | 0.067 | 0.059 | 0.064 |
| 5 | 0.020 | 0.069 | 0.042 | 0.062 | 0.076 | 0.062 | 0.127 | 0.061 |
| 6 | 0.063 | 0.064 | 0.113 | 0.069 | 0.159 | 0.071 | 0.133 | 0.056 |
| 7 | 0.111 | 0.063 | 0.131 | 0.066 | 0.158 | 0.063 | 0.175 | 0.058 |
| 8 | 0.114 | 0.062 | 0.172 | 0.069 | 0.225 | 0.058 | 0.215 | 0.059 |
| 9 | 0.164 | 0.059 | 0.144 | 0.056 | 0.223 | 0.055 | 0.232 | 0.060 |
| 10 | 0.187 | 0.063 | 0.184 | 0.056 | 0.266 | 0.061 | 0.300 | 0.057 |

Figure 3C:
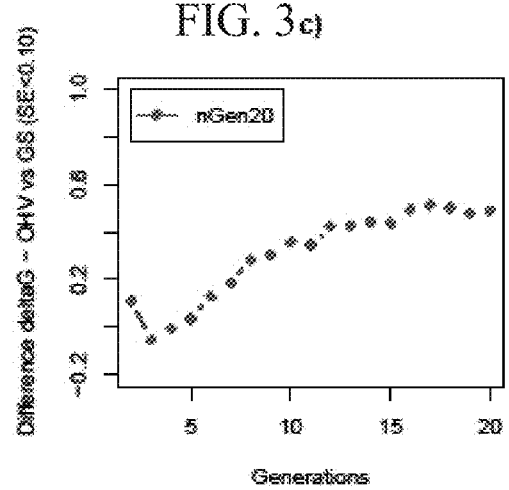

As the breeding programs progressed through generations, OHV increasingly outcompeted GS to yield additional genetic gain (i.e., the advantage of OHV increased when the number of progeny per parent pair increased, and when the number of generations increased), which further underlined the need to accumulate and combine recombination and selection events to maximize genetic gain. The potential advantage of OHV over time was further investigated in a scenario where selection was over 20 generations and it continued up to approximately 16 generations where it appears to asymptote and remain relatively constant. FIG. 3c; Table 5. Even in the early generations, the gain achieved was large, and by generation 10, the genetic gain had almost tripled from OHV selection with 1000 offspring per pair. Again, having more offspring was beneficial, but there may have been a marginally reduced benefit in terms of overall genetic gain when moving from 200 to 1000 offspring per breeding pair.

TABLE 5

Difference in genetic gain between OHV and GS over 20 generations.

| Gen | nGen20 | SE nGen20 |
| --- | --- | --- |
| 2 | 0.110 | 0.087 |
| 3 | −0.052 | 0.095 |
| 4 | −0.004 | 0.085 |
| 5 | 0.035 | 0.079 |
| 6 | 0.129 | 0.086 |
| 7 | 0.186 | 0.090 |
| 8 | 0.284 | 0.098 |
| 9 | 0.305 | 0.085 |
| 10 | 0.358 | 0.075 |
| 11 | 0.346 | 0.079 |
| 12 | 0.422 | 0.078 |
| 13 | 0.425 | 0.076 |
| 14 | 0.441 | 0.076 |
| 15 | 0.435 | 0.081 |
| 16 | 0.493 | 0.069 |
| 17 | 0.511 | 0.075 |
| 18 | 0.502 | 0.067 |
| 19 | 0.478 | 0.066 |
| 20 | 0.489 | 0.071 |

Figure 3D:
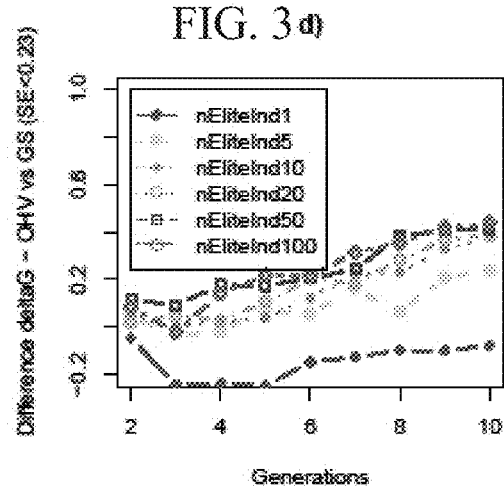

The number of elite individuals chosen for doubled haploid production affected the superiority of OHV less than the number of offspring per cross, and it also depended on the relative superiority of the selected top individuals to the next group of top ranked individuals. We found an increase in the difference between OHV and GS when the number of elite plants was increased. FIG. 3d; Table 6. The top group was similar in genetic merit, and selecting more of them will increase the probability (by chance) that a doubled haploid will achieve a genetic value close to the OHV of the elite individual.

TABLE 6

Difference in genetic gain between OHV and GS when varying the number of elite individuals used for doubled haploid production (nEliteInd).

| Gen | nEliteInd1 | SE nEliteInd1 | nEliteInd5 | SE nEliteInd5 | nEliteInd10 | SE nEliteInd10 |
|---|---|---|---|---|---|---|
| 2 | −0.046 | 0.228 | 0.045 | 0.166 | 0.059 | 0.131 |
| 3 | −0.242 | 0.211 | −0.031 | 0.164 | −0.001 | 0.131 |
| 4 | −0.236 | 0.215 | −0.016 | 0.141 | 0.024 | 0.136 |
| 5 | −0.244 | 0.206 | 0.075 | 0.141 | 0.039 | 0.138 |
| 6 | −0.148 | 0.203 | 0.056 | 0.156 | 0.125 | 0.127 |
| 7 | −0.126 | 0.184 | 0.161 | 0.145 | 0.222 | 0.125 |
| 8 | −0.097 | 0.174 | 0.066 | 0.127 | 0.228 | 0.124 |
| 9 | −0.099 | 0.199 | 0.209 | 0.131 | 0.328 | 0.117 |
| 10 | −0.077 | 0.139 | 0.240 | 0.122 | 0.374 | 0.126 |

| Gen | nEliteInd20 | SE nEliteInd20 | nEliteInd50 | SE nEliteInd50 | nEliteInd100 | SE nEliteInd100 |
|---|---|---|---|---|---|---|
| 2 | 0.021 | 0.120 | 0.118 | 0.106 | 0.083 | 0.094 |
| 3 | 0.049 | 0.155 | 0.091 | 0.132 | −0.020 | 0.124 |
| 4 | 0.029 | 0.125 | 0.178 | 0.121 | 0.141 | 0.121 |
| 5 | 0.105 | 0.130 | 0.174 | 0.119 | 0.218 | 0.101 |
| 6 | 0.205 | 0.134 | 0.206 | 0.129 | 0.214 | 0.125 |
| 7 | 0.181 | 0.119 | 0.244 | 0.115 | 0.313 | 0.115 |
| 8 | 0.280 | 0.119 | 0.380 | 0.115 | 0.355 | 0.095 |
| 9 | 0.366 | 0.114 | 0.408 | 0.107 | 0.418 | 0.103 |
| 10 | 0.386 | 0.113 | 0.412 | 0.098 | 0.436 | 0.108 |

Cycling elite doubled haploids back into the breeding program had a minor effect in terms of the difference between OHV and GS. Table 7. It did not affect overall genetic gain substantially (data not shown). The effect of cycling on the genetic gain is reduced because there is a time-lag before double haploids could be incorporated back into the breeding program. As their production cannot be completed quickly enough to include them in the next generation of crosses, they can only be incorporate two generations later. In the meantime, the crossing population had gone through another round of selection, and its elite individuals were similar in genetic merit to the doubled haploids from two generations ago, leading to a suggestive additional improvement trend for OHV.

genetic variance also indicates how much genetic gain can be achieved via selection. All selection efforts will reduce the genetic variance. However, some methods achieve short term genetic gain at the expense of long-term gain, because they result in severe reduction of the variance, making selection in future generations more difficult to achieve.

Figure 4:
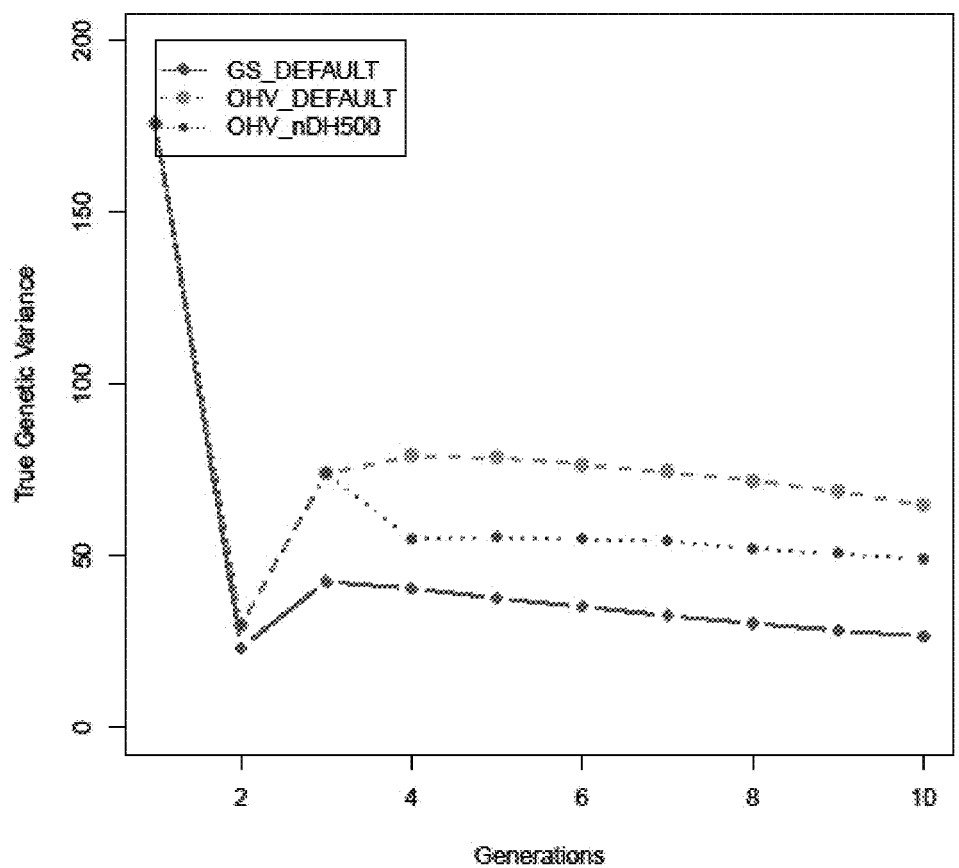
FIG. 4 includes a graphical representation illustrating the true genetic variance in each generation when selection was OHV or genomic breeding values (GS) for DEFAULT and nDH500 scenarios (SE<3.64).

A key advantage of OHV selection is its ability to maintain more genetic variation or diversity in the population than GS. This is strongly demonstrated in FIG. 4 and Table 8. The true genetic variance was highest in the unselected base population. First, it declined sharply because only the top 30% of lines were used to generate a completely heterozygous $F_1$ generation. Crossing the $F_1$ then released additional genetic variation, because homozygous

TABLE 7

Difference in genetic gain between OHV and GS when varying the number of elite doubled haploids cycled back into the breeding program (nDHcyc).

| Gen | nDHcyc0 | SE n0 | nDHcyc10 | SE n10 | nDHcyc20 | SE n20 | nDHcyc50 | SE n50 |
|---|---|---|---|---|---|---|---|---|
| 2 | 0.059 | 0.131 | 0.059 | 0.131 | 0.059 | 0.131 | 0.059 | 0.131 |
| 3 | −0.001 | 0.131 | −0.001 | 0.131 | −0.001 | 0.131 | −0.001 | 0.131 |
| 4 | 0.050 | 0.132 | 0.018 | 0.136 | 0.079 | 0.132 | 0.024 | 0.136 |
| 5 | 0.129 | 0.132 | 0.009 | 0.126 | 0.064 | 0.125 | 0.039 | 0.138 |
| 6 | 0.076 | 0.130 | 0.174 | 0.122 | 0.093 | 0.134 | 0.125 | 0.127 |
| 7 | 0.158 | 0.121 | 0.239 | 0.126 | 0.165 | 0.122 | 0.222 | 0.125 |
| 8 | 0.218 | 0.125 | 0.169 | 0.116 | 0.173 | 0.123 | 0.228 | 0.124 |
| 9 | 0.231 | 0.134 | 0.296 | 0.134 | 0.293 | 0.135 | 0.328 | 0.117 |
| 10 | 0.266 | 0.119 | 0.333 | 0.136 | 0.349 | 0.118 | 0.374 | 0.126 |

| Gen | nDHcyc80 | SE 80 | nDHcyc100 | SE 100 | nDHcyc200 | SE 200 | nDHcyc500 | SE 500 |
|---|---|---|---|---|---|---|---|---|
| 2 | 0.059 | 0.131 | 0.059 | 0.131 | 0.059 | 0.131 | 0.059 | 0.131 |
| 3 | −0.001 | 0.131 | −0.001 | 0.131 | −0.001 | 0.131 | −0.001 | 0.131 |
| 4 | 0.057 | 0.138 | 0.038 | 0.131 | 0.014 | 0.126 | 0.009 | 0.138 |
| 5 | 0.085 | 0.154 | 0.069 | 0.134 | 0.079 | 0.129 | 0.037 | 0.128 |
| 6 | 0.138 | 0.146 | 0.130 | 0.133 | 0.091 | 0.150 | 0.102 | 0.127 |
| 7 | 0.181 | 0.136 | 0.182 | 0.122 | 0.186 | 0.145 | 0.140 | 0.127 |
| 8 | 0.206 | 0.120 | 0.279 | 0.138 | 0.177 | 0.137 | 0.169 | 0.128 |
| 9 | 0.298 | 0.134 | 0.248 | 0.112 | 0.306 | 0.123 | 0.187 | 0.134 |
| 10 | 0.316 | 0.112 | 0.317 | 0.109 | 0.301 | 0.117 | 0.224 | 0.111 |

The genetic variance in population is a parameter that provides a measure of the diversity in the population. The genotypes were now also observed. In generation three, the true genetic variance of OHV selection was almost twice that of GS. Furthermore, OHV selection reduced the genetic variance at a slower pace than GS in subsequent generation, and OHV diversity was almost 200% greater by generation 10. Note that cycling 500 doubled haploids back into the breeding program reduced the genetic variance substantially in generation four, because segregating individuals were replaced with doubled haploids generated from 10 heavily selected elites resulting in a significant narrowing of the genetic base. Incidentally, this scenario also showed the smallest difference in genetic gain between OHV and GS. Table 7.

TABLE 8

True breeding value variance per generation in GS or OHV breeding programs.

| Gen | GS DEFAULT | GS DEFAULT | OHV DEFAULT | SE OHV DEFAULT |
|---|---|---|---|---|
| 2 | 175.690 | 0.366 | 175.690 | 3.639 |
| 3 | 23.246 | 0.073 | 29.741 | 0.800 |
| 4 | 42.556 | 0.078 | 74.094 | 1.102 |
| 5 | 40.526 | 0.066 | 79.042 | 1.013 |
| 6 | 37.736 | 0.059 | 78.516 | 0.964 |
| 7 | 35.212 | 0.052 | 76.654 | 0.906 |
| 8 | 32.654 | 0.050 | 74.392 | 0.905 |
| 9 | 30.344 | 0.044 | 71.949 | 0.880 |
| 10 | 28.294 | 0.042 | 68.766 | 0.872 |

| Gen | GS nDH0 | SE GS nDH0 | OHV nDH0 | SE OHV nDH0 | OHV nDH500 | SE nDH500 |
|---|---|---|---|---|---|---|
| 2 | 175.690 | 0.366 | 175.690 | 0.366 | 175.690 | 3.639 |
| 3 | 23.246 | 0.073 | 29.741 | 0.080 | 29.741 | 0.800 |
| 4 | 42.556 | 0.078 | 74.094 | 0.111 | 74.094 | 1.102 |
| 5 | 38.585 | 0.061 | 75.451 | 0.094 | 54.978 | 0.699 |
| 6 | 35.699 | 0.056 | 75.086 | 0.091 | 55.451 | 0.734 |
| 7 | 32.393 | 0.049 | 73.701 | 0.090 | 54.751 | 0.712 |
| 8 | 29.172 | 0.045 | 71.530 | 0.089 | 54.213 | 0.750 |
| 9 | 26.015 | 0.041 | 68.097 | 0.086 | 52.197 | 0.739 |
| 10 | 23.066 | 0.037 | 64.525 | 0.080 | 50.611 | 0.743 |

One reason for this outcome can be explained with a perhaps extreme example. Assume an individual carries one haplotype that is superior, and another that is poor, at every segment on its genome. It could therefore be classified as a "highly variable" individual. OHV selection would select it, because its OHV would be very high. However, GS would likely not select this individual, because its GEBV is the sum of all allele effects. Due to this fact, GS selects for high merit individuals with low variability, whereas OHV will select regardless of variability within the individual.

Population genetic diversity is particularly important for long-term genetic gain. One disadvantage of strong selection pressure without regard to diversity or inbreeding is that low frequency variants are lost. Jannink (2010) Genet. Select. Evol. 42:35. Maintaining low frequency alleles or haplotypes in the population longer allows for selection to slowly increase their frequency until they explain a larger proportion of the genetic variance. OHV selection, through its selection on one haplotype rather than on the sum of the two haplotypes, maintains low frequency variants longer. The increasing advantage of OHV at later generations is a manifestation of increased long-term genetic gain that is expected to be directly due to its greater genetic variance carried in the breeding population. Our study demonstrates that a clear breeding strategy that preserves genetic diversity results in more long-term genetic gain.

Reducing selection pressure away from the sum of the haplotypes to individual haplotypes also allows for more efficient multi-trait selection programs. It allows favorable haplotypes to be maintained, even when they are in trans, thereby providing more opportunities for crop improvement. For example, an individual undergoing GS selection carrying a favorable disease resistance allele in one haplotype and a favorable yield allele in the other haplotype in the same genomic segment is likely to result in the selection of only one haplotype due to the two segments explicitly competing. In contrast, OHV selection allows both haplotypes to be maintained more easily in the breeding population, thus increasing the probability that in time a recombination event will combine both favorable alleles in the same haplotype.

Figure 5A:
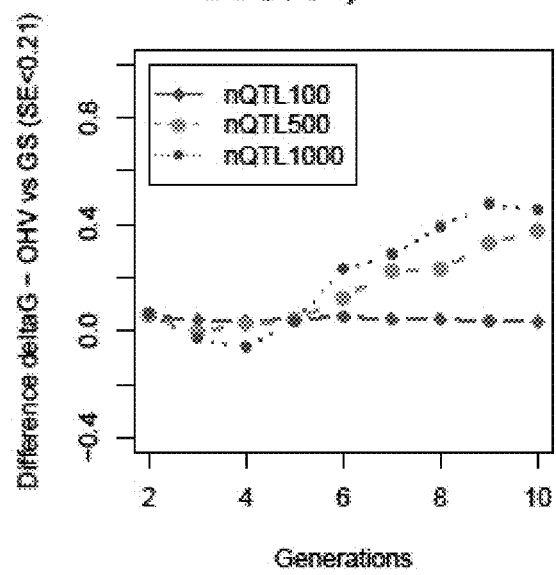
FIGS. 5a-5b includes a graphical representation illustrating the difference in genetic gain (deltaG) between OHV and GS when the number of QTL is varied (nQTL) (FIG. 5a), or the number of haplotype segments per chromosome is varied (nSeg) (FIG. 5b).

To investigate the effect of genetic architecture on the relative gain from OHV versus GS, we simulated three different genetic architectures of 100, 500, or 1000 QTL. The use of OHV was advantageous regardless of the number of QTL affecting the trait. FIG. 5a; Table 9. The advantage with OHV was small and consistent across generations with 100 QTL. When 500 or 1000 QTL were simulated a slight depression of OHV versus GS was observed which was overcome by generation 5, after which OHV again consistently performed better than GS. The sustained gain in performance was larger as the trait became more polygenic.

TABLE 9

Difference in genetic gain between OHV and GS when varying the number of QTL (nQTL).

| Gen | nQTL100 | SE nQTL100 | nQTL500 | SE nQTL500 | nQTL1000 | SE nQTL1000 |
|---|---|---|---|---|---|---|
| 2 | 0.056 | 0.058 | 0.059 | 0.131 | 0.065 | 0.211 |
| 3 | 0.042 | 0.049 | −0.001 | 0.131 | −0.031 | 0.184 |
| 4 | 0.036 | 0.043 | 0.024 | 0.136 | −0.061 | 0.191 |
| 5 | 0.046 | 0.036 | 0.039 | 0.138 | 0.035 | 0.191 |
| 6 | 0.053 | 0.035 | 0.125 | 0.127 | 0.230 | 0.208 |
| 7 | 0.045 | 0.034 | 0.222 | 0.125 | 0.286 | 0.206 |
| 8 | 0.045 | 0.026 | 0.228 | 0.124 | 0.394 | 0.190 |
| 9 | 0.038 | 0.023 | 0.328 | 0.117 | 0.474 | 0.215 |
| 10 | 0.035 | 0.023 | 0.374 | 0.126 | 0.453 | 0.174 |

Figure 5B:
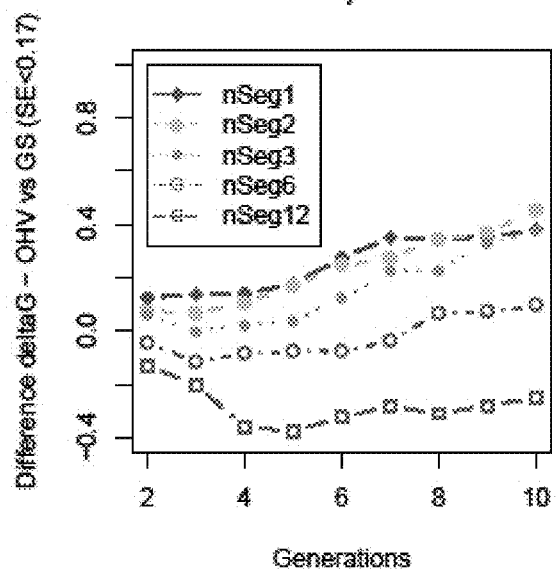

The sensitivity of the results to the length of the haplotype or genome segment considered were tested by testing each chromosome as its own separate segment or dividing each into 2, 3, 6, or 12 segments. OHV selection performed better than GS when the number of segments was 3 or less. The base scenario had 3 segments per chromosome and showed a reduction in the difference between OHV and GS in generation 3, 4, and 5. FIG. 5b; Table 10. This reduction was avoided when chromosomes were only divided in two or left intact.

TABLE 10

Difference in genetic gain between OHV and GS when varying the number of segments (nSeg).

| Gen | nSeg1 | SE nSeg1 | nSeg2 | SE nSeg2 |
|---|---|---|---|---|
| 2 | 0.125 | 0.138 | 0.077 | 0.135 |
| 3 | 0.136 | 0.154 | 0.067 | 0.142 |
| 4 | 0.141 | 0.124 | 0.108 | 0.144 |
| 5 | 0.175 | 0.122 | 0.169 | 0.142 |
| 6 | 0.274 | 0.122 | 0.246 | 0.125 |
| 7 | 0.349 | 0.116 | 0.274 | 0.148 |
| 8 | 0.345 | 0.126 | 0.345 | 0.129 |
| 9 | 0.352 | 0.129 | 0.369 | 0.110 |
| 10 | 0.380 | 0.115 | 0.450 | 0.120 |

| Gen | nSeg3 | SE nSeg3 | nSeg6 | SE nSeg6 | nSeg12 | SE nSeg12 |
|---|---|---|---|---|---|---|
| 2 | 0.059 | 0.131 | −0.046 | 0.136 | −0.130 | 0.166 |
| 3 | −0.001 | 0.131 | −0.115 | 0.145 | −0.201 | 0.155 |
| 4 | 0.024 | 0.136 | −0.085 | 0.133 | −0.359 | 0.141 |
| 5 | 0.039 | 0.138 | −0.073 | 0.147 | −0.375 | 0.150 |
| 6 | 0.125 | 0.127 | −0.078 | 0.132 | −0.324 | 0.133 |
| 7 | 0.222 | 0.125 | −0.038 | 0.155 | −0.280 | 0.144 |
| 8 | 0.228 | 0.124 | 0.068 | 0.137 | −0.310 | 0.125 |
| 9 | 0.328 | 0.117 | 0.070 | 0.138 | −0.279 | 0.125 |
| 10 | 0.374 | 0.126 | 0.096 | 0.151 | −0.249 | 0.135 |

We simulated a mean recombination rate of one per Morgan. A large number of individuals will not have any (or very few) recombinations per chromosome, and, therefore, a model with few segments would be most similar. Increasing the number of segments increases the OHV of a particular individual, because haplotypes can be more finely combined in silico to create an elite plant. However, this OHV cannot be achieved in one generation of doubled haploidy. In essence, the 12 segment OHV is the plant that may be achieved in excess of six or more generations of accumulating recombinations. This causes a drift away from the selection goal of picking the plant that can achieve the best doubled haploid in one cycle of selection to the plant that may produce the best doubled haploid several generations later, decreasing the benefit of OHV over GS.

Example 3: OHV Selection During Introgression

A breeding program combining OHV and introgression was performed in silico using an elite wheat line that includes five events (i.e., a highly transformable line with five EXZACT™ genome modifications), which was crossed with the same elite wheat base population described in Example 1 to simultaneously introgress the five event loci. For the next 5 generations (approximately the time taken to recover the original background after an introgression), the plants with the highest OHV that also carry at least one introgression allele at each introgression locus were selected for doubled haploid production. When 100 doubled haploids were produced, most of the selected haploid lines produced several doubled haploids fixed at all introgressions.

Figure 6:
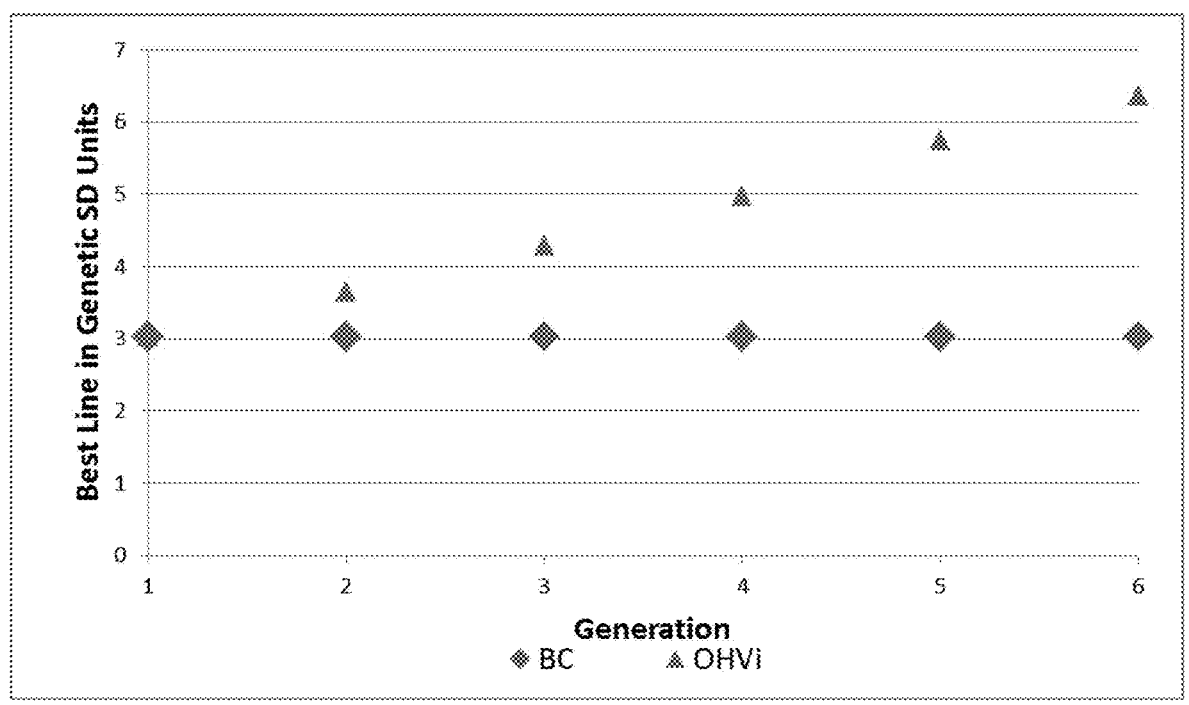
FIG. 6 includes a graphical representation illustrating advantages of OHV-based introgression (including increased genetic gain) over traditional introgression to recover the original genetic background.

FIG. 6 shows the difference between traditional introgression (GS) and introgression combined with OHV selection (mean of 100 replicates). While the genetic value using traditional introgression remained the same, increases in genetic gain were achieved using OHVi. OHVi selection is expected to achieve genetic gains exceeding those produced by GSi when the number of crosses and offspring per generation is increased.

A function (OHVi) was established that combines values for OHV and speed of introgressing one or more desired events into a population. OHVi is the sum of OHV and the weighted value of the desired introgressions. OHVi is useful for increasing the introgression of particular allele frequencies in the population, while also maximizing OHV in the population, thereby achieving maximum genetic gain. Generally, OHVi balances the value of obtaining introgression events and the value of OHV, and can be expressed as:

$$OHVi = OHV + iEmphasis(w_1 x_1 + w_2 x_2 + w_3 x_3),$$

where iEmphasis is the overall weight placed on introgression, $w_n$ (e.g., $w_1$, $w_2$, and $w_3$) corresponds to the weight placed on introgression allele n and $x_n$ (e.g., x1, x2, and x3) is the number of introgression alleles (e.g., 0, 1, or 2 in a diploid). Each $w_n$ = [desired frequency of the introgression allele] − [actual frequency of the introgression allele].

Thus, the variable iEmphasis governs the speed of introgression, and adjusting its values ensures that the complimentary goals of maximizing OHV and introgression are best met. The weighting of introgression alleles ($w_n$) are selected to provide the most emphasis to low frequency alleles that are at the greatest distance from the desired allele frequency. This fitness function could be applied at the level of the individuals as described above or at the level of the selected group. For example, a genetic algorithm can be applied to select the best group of individuals to be used as parents in the next generation to maximize genetic gain and achieve desired introgressions.

Example 4: OHV Selection in Empirical Maize Genotypes

Data. The data pool used included empirical genotypes for 23,981 single nucleotide polymorphisms (SNP) for 900 inbred maize lines from two heterotic groups. A linkage map provided genomic order and distance information in centi-Morgans (cM). There were 10 chromosomes and total length of the linkage map was 1748 cM. SNP effect estimates were available from a conventional genomic selection method study. Habier et al. (2011), supra; Meuwissen et al. (2001), supra. SNP effects were available from two heterotic groups.

Simulations. Two simulation streams were performed: 1) Empirical SNP genotypes were used as the base population and SNP effects were sampled from a double exponential distribution (Stream 1), 2) Empirical SNP genotypes and empirical SNP effects were used in the analysis (Stream 2).

Base Population Genomes. Computer simulations were performed to compare genomic selection and OHV selection in Maize. The empirical SNP were placed on 10 chromosomes according to the linkage map and each chromosome measured 170 cM. Cross-overs were randomly placed on the genome at a rate of 1 per Morgan during the creation of gametes, either in conventional offspring or during creation of doubled haploids. Various haplotype or OHV segment lengths were investigated.

Simulated Breeding Program. Two breeding scenarios were simulated: GS, where selection was based on genomic breeding values (GEBV) and OHV, where selection was based on optimal haploid values. All parameters, such as selection intensity, were the same between GS and OHV and the only difference was that selection was either on GEBV or OHV.

Figure 7:
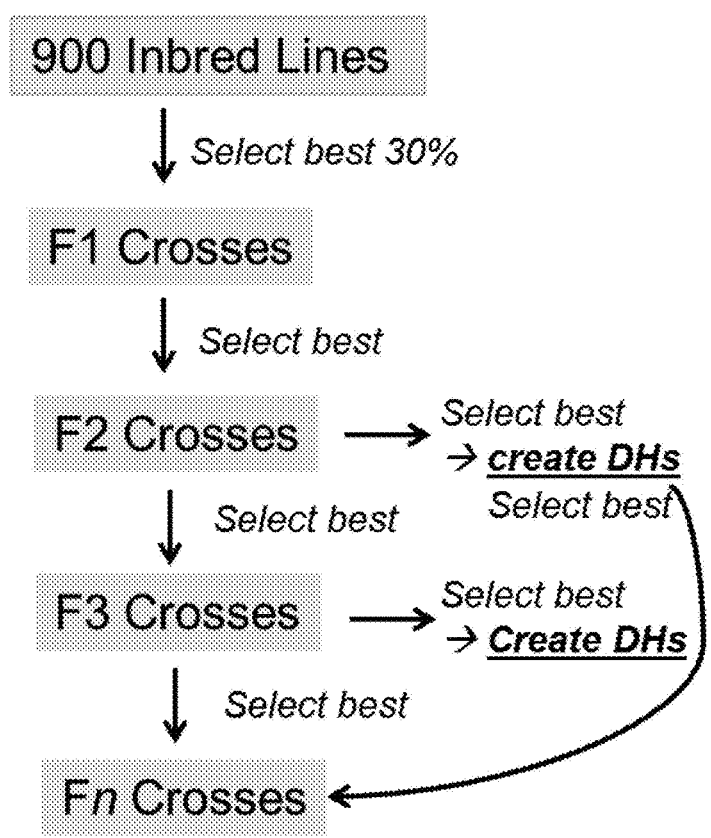
FIG. 7 includes a graphical representation illustrating a generic genomic breeding program in maize design for "stream 1," where DH is doubled haploid, and n is number of generations. Selection is based on either on optimal haploid or genomic estimated breeding value. Elite doubled haploids can be cycled back into breeding population in the second generation after creation.

The generic breeding program was as follows (specific scenarios are described subsequently). In stream 1, the best 30% of the initial inbred 900 lines were used as parents of the F1 generation to achieve a population size of 36,000 individuals. FIG. 7. In stream 2, parents from heterotic groups were run separately (506 group 1, 394 group 2) and 60% of base generation individuals were selected. Every selected inbred line was crossed with all other selected lines.

One progeny was then genotyped per cross (as all were identical) and the top individuals were selected to produce the next generation (F2). In the outbred F2 to F10 generations each individual was only mated to one other individual, as under limited seed conditions. All mating was random. The number of offspring per outbred cross was varied and the total breeding population was kept constant at 27,000 to 36,000 individuals (depending on stream) by varying selection intensity. In each generation, the most elite plants were selected for doubled haploid production and a varied number of doubled haploids was produced. The most elite doubled haploids could optionally be used for breeding two generations later to account for the time-lag for creation and doubled haploid seed collection. This was then repeated for several generations and, in each generation, OHV and GEBV were recalculated, which captured new recombination events.

Results. In the DEFAULT scenario 100 offspring were produced per outbred cross, 10 elite individuals were selected to create 100 doubled haploids each and the best 50 doubled haploids were cycled back into the breeding program. The breeding program duration was 10 generations. Various scenarios investigated the number of: offspring produced per outbred cross (nOff), doubled haploids produced per elite individual (nDH), elite doubled haploids cycled back into the breeding program two generations later (nDHcycled) and the number of haplotype segments per chromosome (nSeg). All scenario groups and levels within are listed in Table 11. The results on genetic gain focus on the difference between OHV and GS in genetic standard deviations (SD) of the base generation (i.e., gain OHV−gain GS). Since the genetic variance is substantially larger in the base, this is a conservative measure. Genetic diversity is reported as the true genetic variance, calculated as the variance of true breeding values in a generation.

TABLE 11

The scenarios groups investigated with description and a list of levels.

| Scenario Group | Variation | Levels |
|---|---|---|
| DEFAULT | Default scenario | nOff 100, nEliteInd 10, nDH 100, nDHcycled 50, nQTL 500, nSeg 3, nGen 10 |
| nOff | Number of offspring per outbred cross | 10, 50, 100, 200, 500, 1000 |
| nDH | Number of DHs produced per elite individual | 10, 50, 100, 200, 500, 1000 |
| nDHcycled | Number of DHs cycled back into breeding program | 0, 20, 50, 100, 200, 500 |
| nSeg | Number of haplotype segments per chromosome | 1, 2, 3, 6 |

Level in bold type relate to the DEFAULT scenario.
Only one parameter was perturbed at a time.

For stream 1, 10 percent of all loci (N=2388) were chosen as quantitative trait loci (QTL) and were selected at random with effects sampled from a double exponential distribution. For both genomic selection and OHV selection, marker effects were assumed to be known and marker effect estimations were not varied as between genomic selection and OHV. The magnitude of total genetic gain achieved in this study is likely to be higher than in actual genomic selection-based breeding programs, where inaccuracy of marker effects can reduce genetic gain. Each scenario was replicated 100 times and standard errors (SE) were calculated.

For stream 2, two sets of empirical estimates of marker effects were used (Heterotic group 1 and 2) and only the genotypes from the respective groups were used (Group 1 506 accessions, Group 2 394 accessions). In both cases all scenarios outlined in Table 1 were run except nDHcycled. 100 replicates were run were scenario to vary locations of recombinations. The distribution of the two sets of marker effects was checked and it was approximately normal (Gaussian). Estimates were taken as true effects, however, they are expected to contain some error. Furthermore, depending on sample size during estimation, they would also be regressed towards the mean affecting their distribution (i.e., very few large effects were observed). SNP markers for which no effects were provided were assumed to have zero effect.

Figure 8:
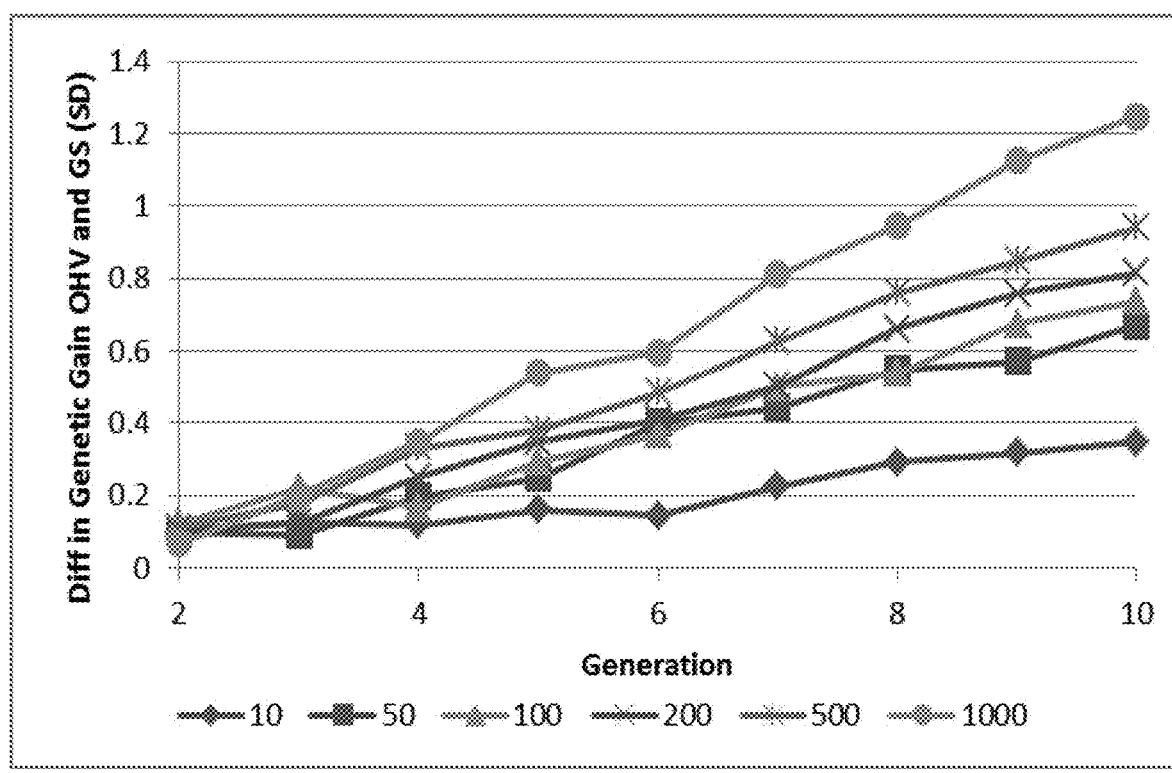
FIG. 8 includes a graphical representation illustrating the difference in genetic gain per generation between OHV and GS when varying the number of offspring per cross (nOff) (10, 50, 100, 200, 500, and 1000) utilizing an empirical marker set from maize. Range of standard error from 0.14 to 0.28, in early to late generations, respectively.

Stream 1. In this stream, empirical maize genotypes were used and SNP effects were sampled from a double exponential distribution. OHV selection resulted in increased genetic gain when compared to genomic selection. This advantage was consistent across all scenarios investigated. The increase in genetic gain was up to 1.2 genetic standard deviation when compared to genomic selection (nOff1000, FIG. 8). The spread between the two methods increased in each subsequent generation and as more offspring were produced per outbred cross.

Figure 9:
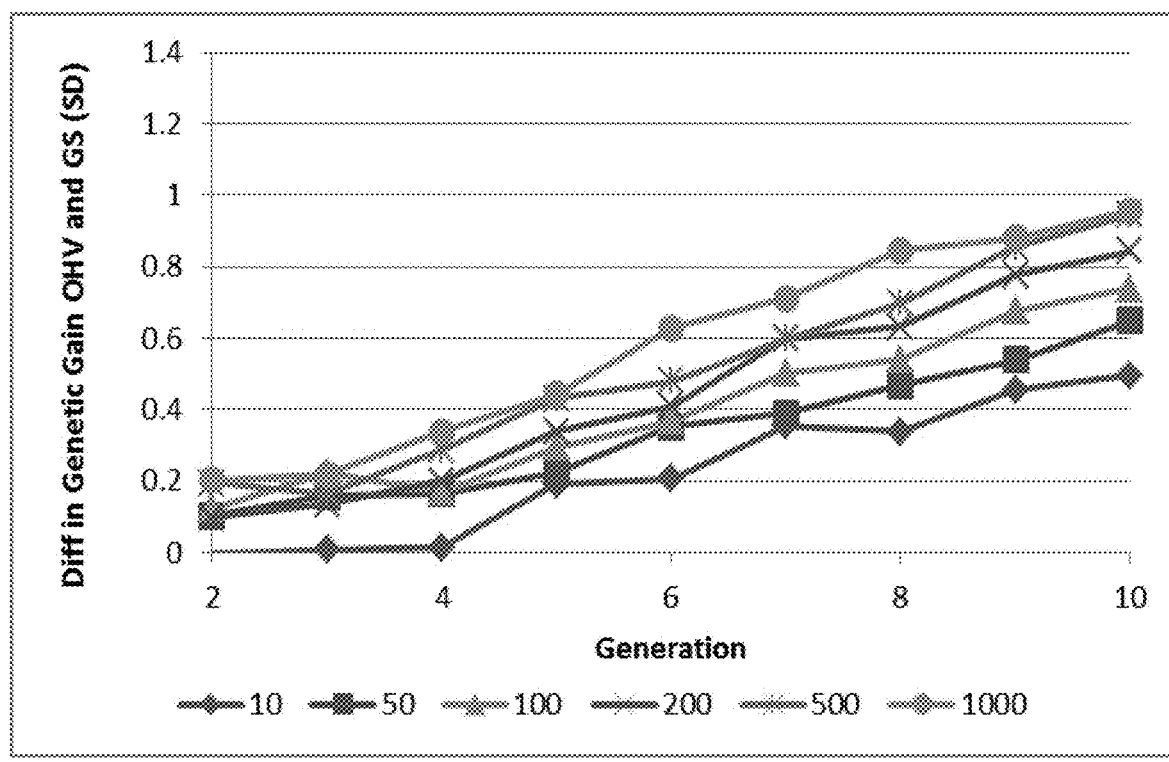
FIG. 9 includes a graphical representation illustrating the difference in genetic gain per generation between OHV and GS when varying the number of doubled haploids produced per elite plant (nDH) nOff) (10, 50, 100, 200, 500, and 1000) utilizing an empirical marker set from maize. Range of standard error from 0.12 to 0.19, in early to late generations, respectively FIG. 10 includes a graphical representation illustrating the difference in genetic gain per generation between OHV and GS when varying the number of elite doubled haploids cycled back into the breeding program (nDHcycled) nOff) (0, 10, 50, 100, 200) utilizing an empirical marker set from maize. Range of standard error from 0.12 to 0.19, in early to late generations, respectively.

Increasing the number of doubled haploids produced per elite plant also increased the genetic gain of OHV selection over genomic selection (nDH, FIG. 9).

Figure 10:
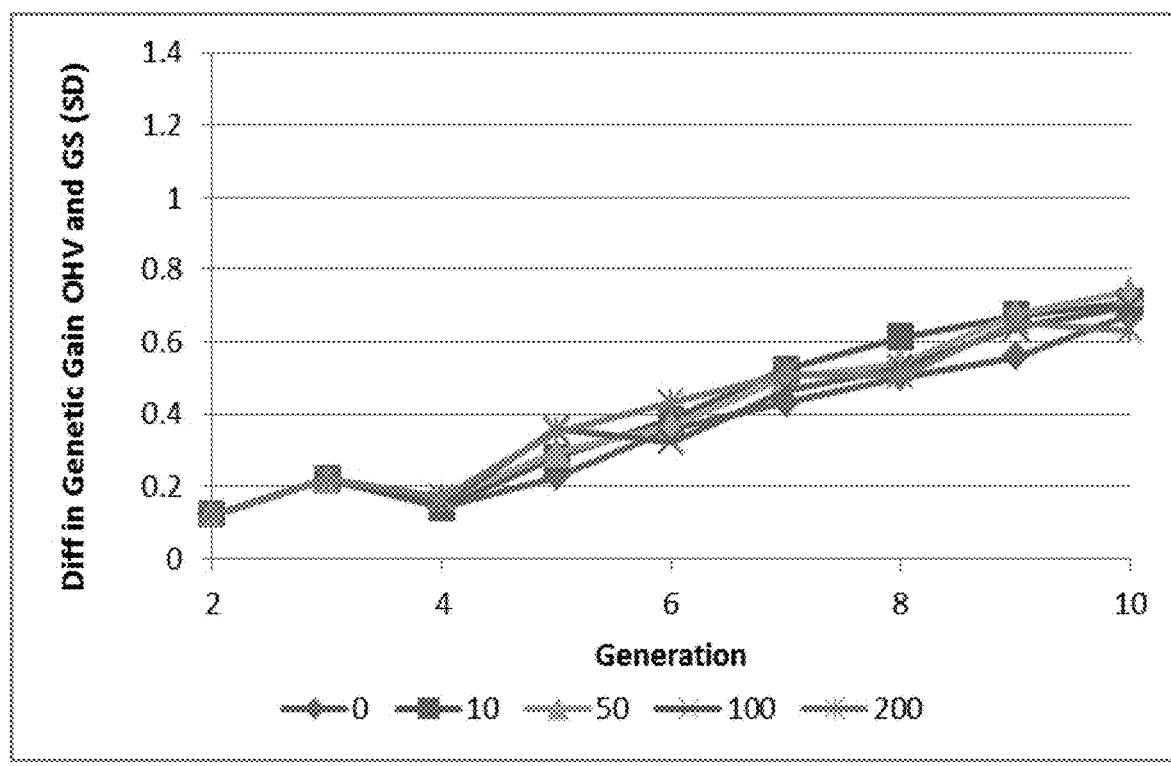

No effect was observed due to cycling a varying number of elite doubled haploids back into the breeding program (nDHcycled, FIG. 10). This is likely due to the crossing population undergoing an additional generation of selection by the time the doubled haploids are added back in, and catching up to the genetic superiority of the elite doubled haploids.

Figure 11:
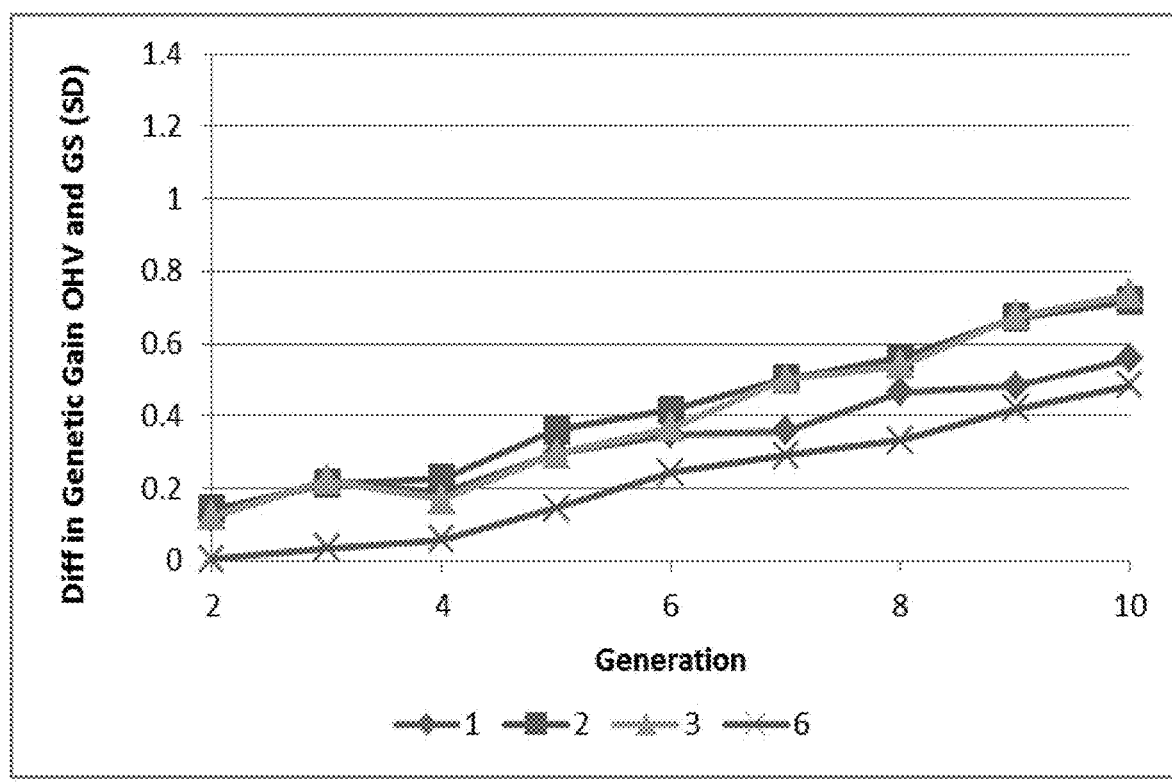
FIG. 11 includes a graphical representation illustrating the difference in genetic gain per generation between OHV and GS when varying the number of haplotype segments per chromosome (nSeg) (1, 2, 3, and 6) utilizing an empirical marker set from maize. Range of standard error from 0.12 to 0.18, in early to late generations, respectively.

In early generations, 1, 2, or 3 segments per chromosome seem superior to 6 segments, though still within SE (nSeg, FIG. 11). In later generations, the results suggest that dividing the chromosome into 2 or 3 segments yields best results.

Figure 12:
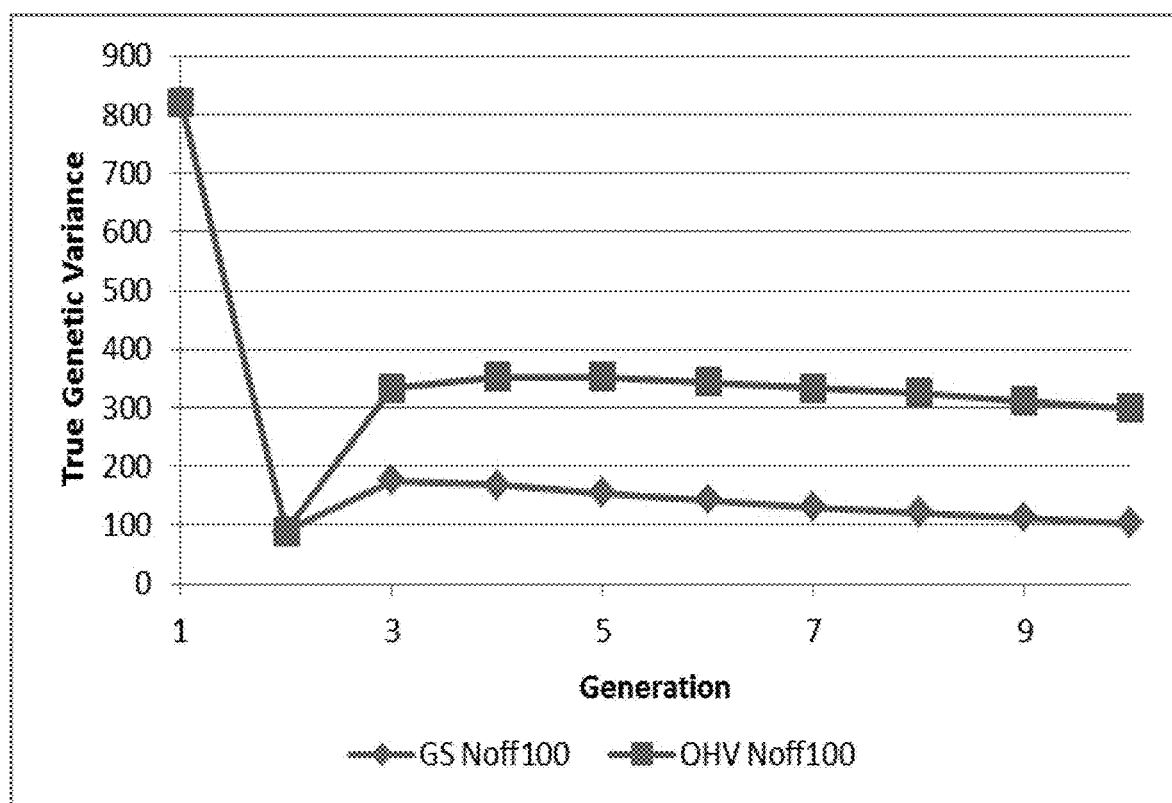
FIG. 12 includes a graphical representation illustrating the true genetic variance per generation of OHV and GS breeding programs utilizing an empirical marker set from maize.
Figure 13:
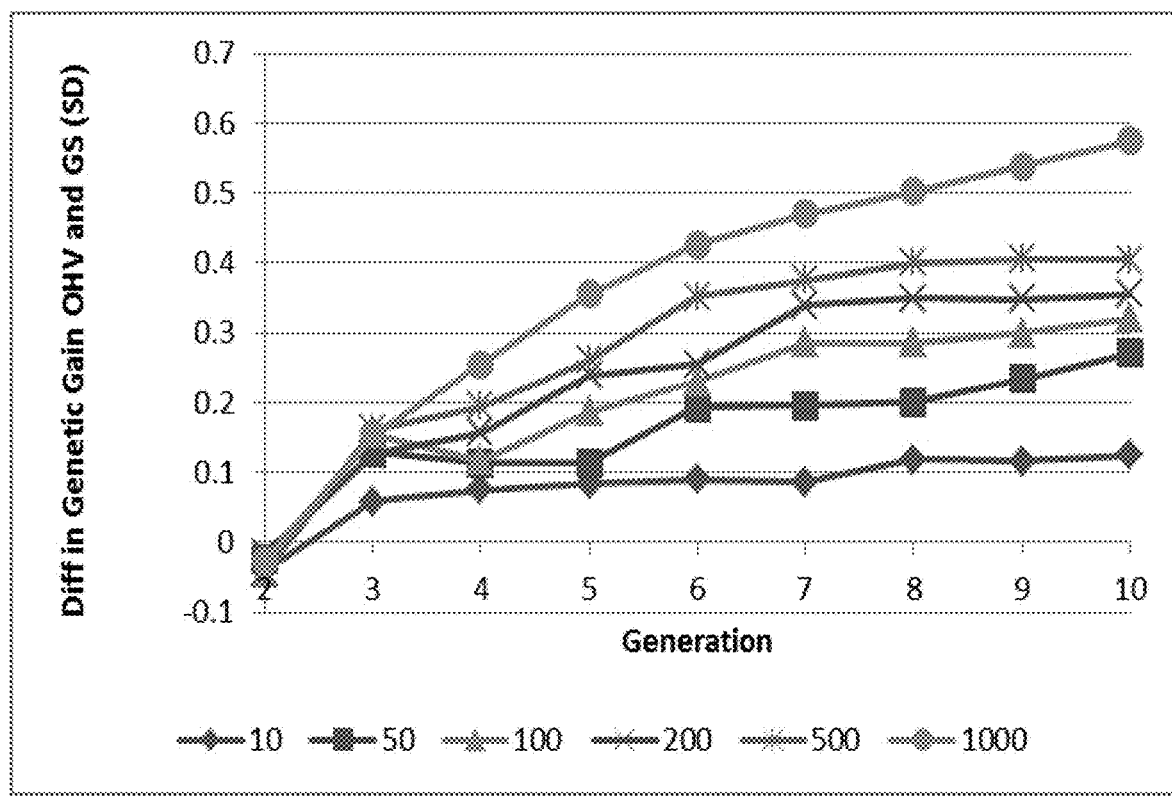
FIG. 13 includes a graphical representation illustrating the difference in genetic gain between OHV and GS when varying the number of offspring per cross (nOff) (10, 50, 100, 200, 500, and 1000) using heterotic group 1 SNP effects in an empirical marker set from maize. Range of standard error from 0.04 to 0.09.
Figure 14:
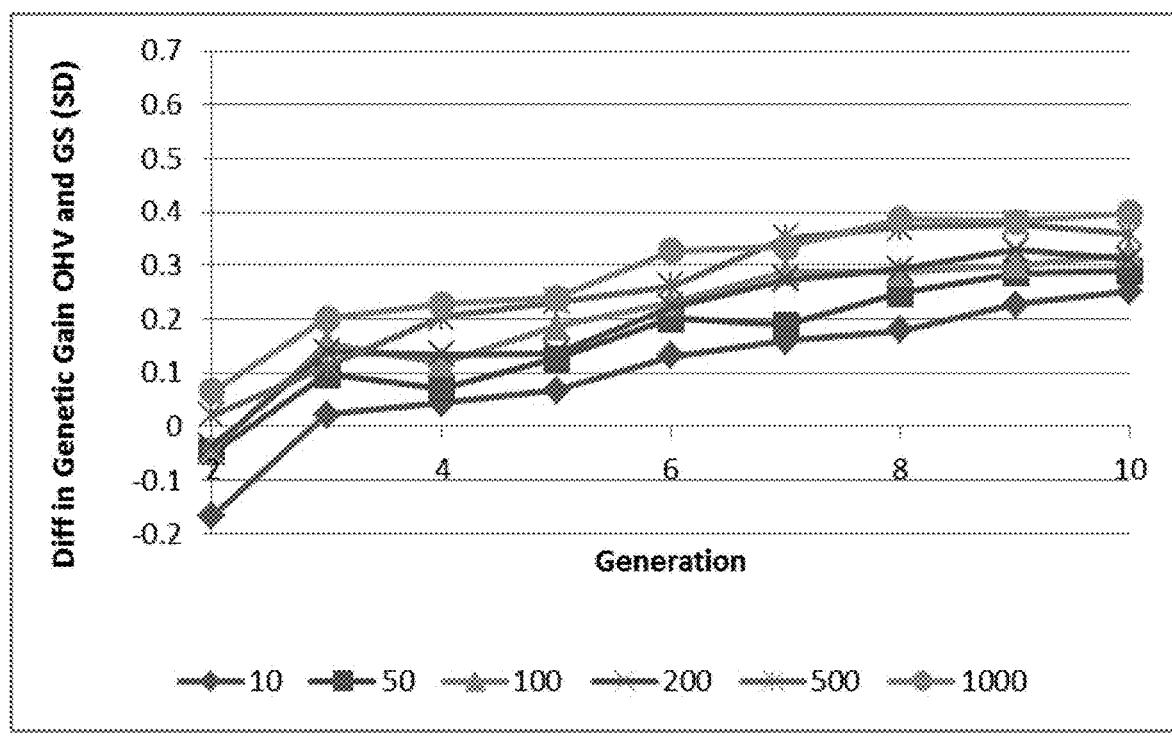
FIG. 14 includes a graphical representation illustrating the difference in genetic gain per generation between OHV and GS when varying the number of doubled haploids produced per elite plant (nDH) using heterotic group 1 SNP effects in an empirical marker set from maize. Range of standard error from 0.04 to 0.09.
Figure 15:
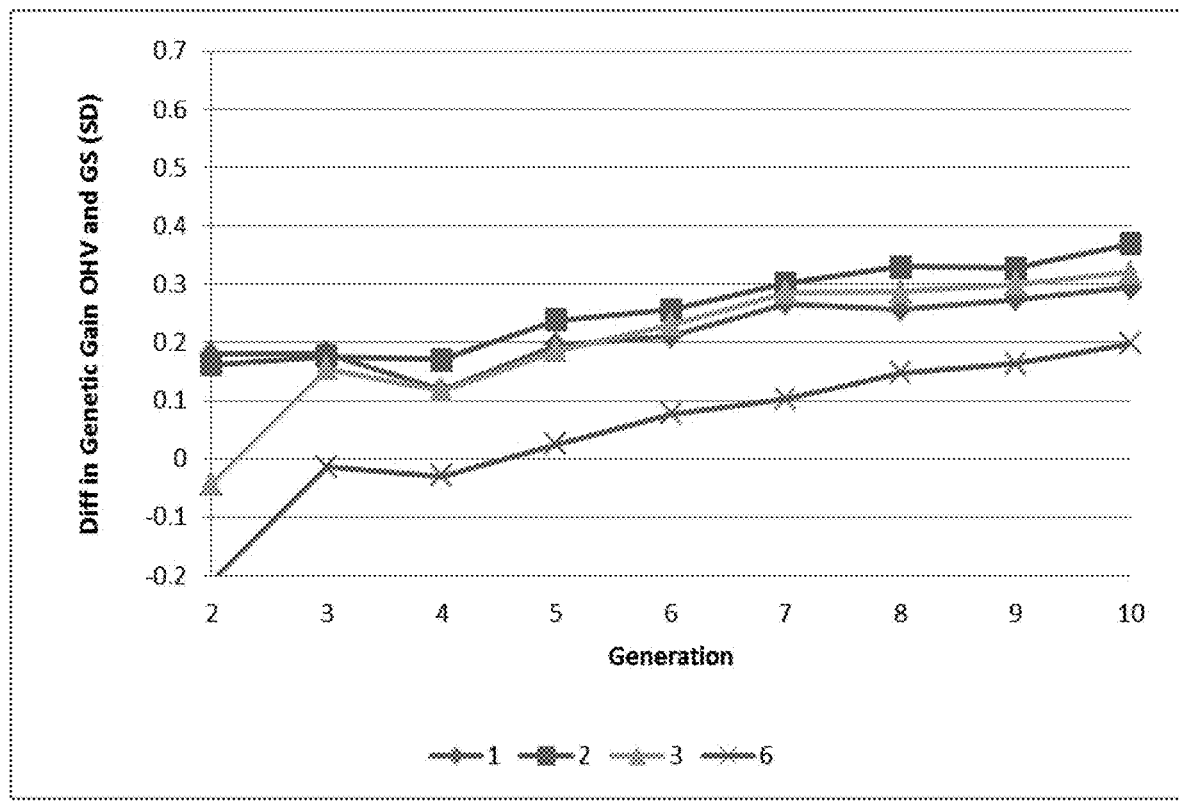
FIG. 15 includes a graphical representation illustrating the difference in genetic gain per generation between OHV and GS when varying the number of haplotype segments per chromosome (nSeg) (1, 2, 3, and 6) using heterotic group 1 SNP effects in an empirical marker set from maize. Range of standard error from 0.04 to 0.09.

The genetic diversity maintained in a population is an important indicator of the long-term genetic gain that can be achieved. The true genetic variance is one indicator of diversity. FIG. 12 clearly demonstrates that OHV selection produced greater genetic variance in the breeding population than genomic selection.

Stream 2. In this stream, empirical genotypes and empirical SNP effects were used in the simulations. There were two sets of SNP effects (Group1 and Group2).

Figure 16:
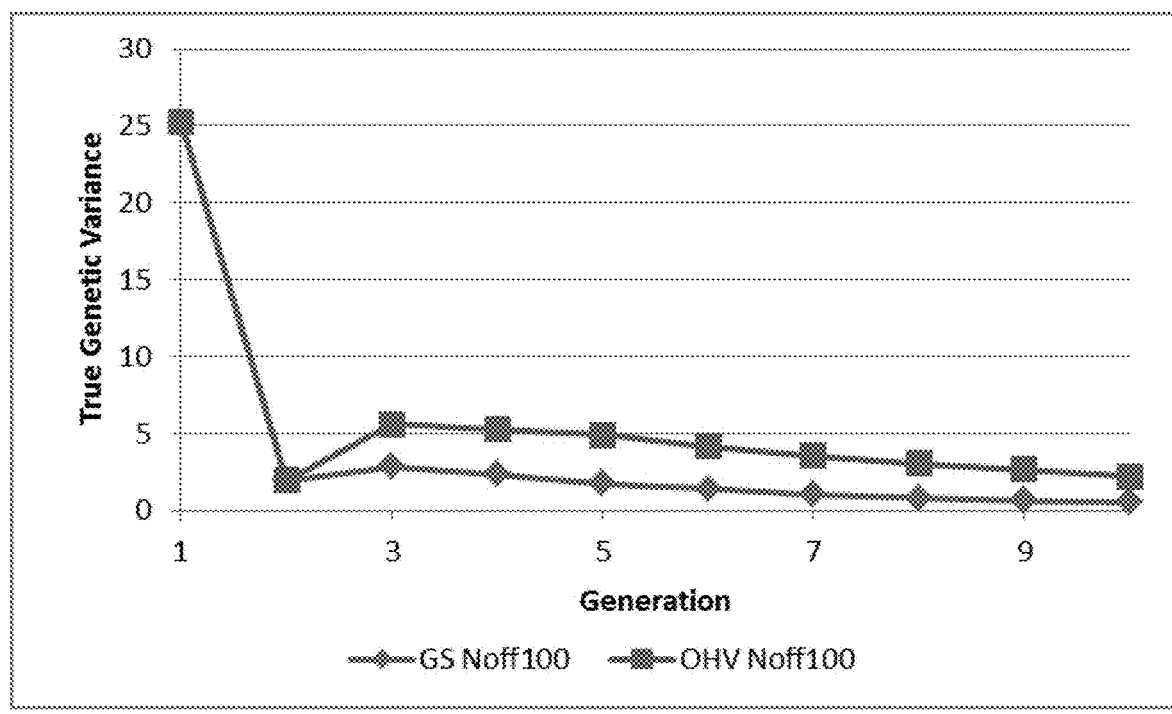
FIG. 16 includes a graphical representation illustrating the true genetic variance per generation of OHV and GS breeding programs and using heterotic group 1 SNP effects in an empirical marker set from maize. Range of standard error from 0.0 to 0.03.
Figure 17:
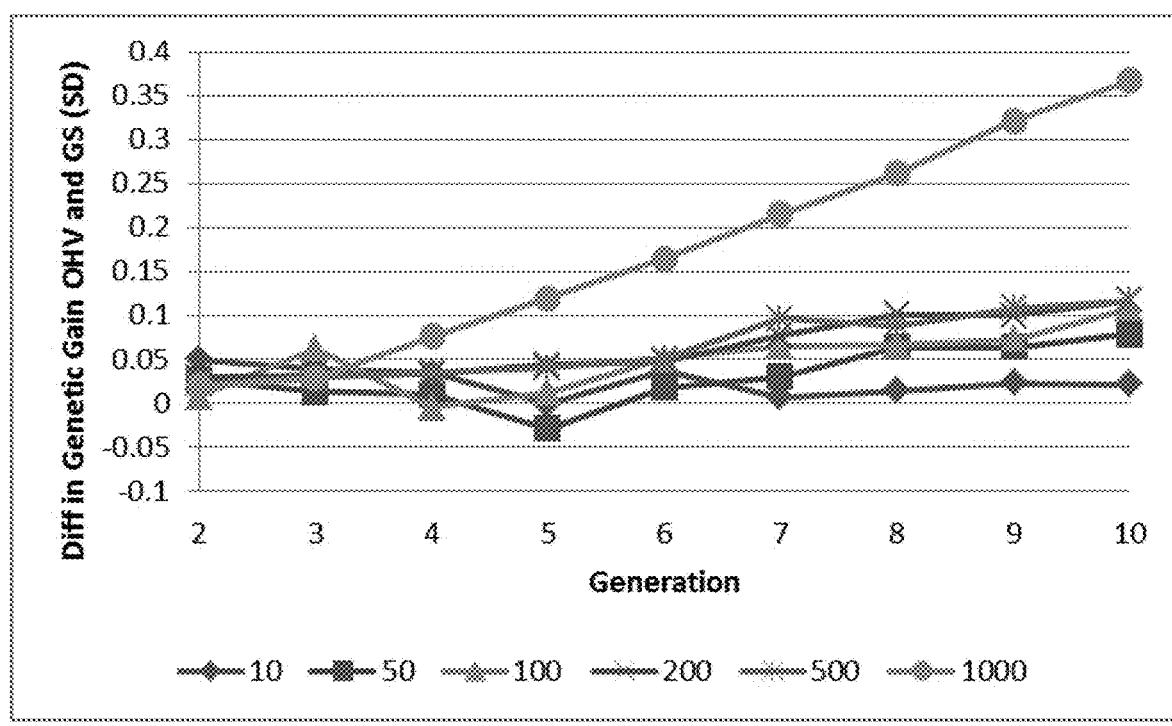
FIG. 17 includes a graphical representation illustrating the difference in genetic gain per generation between OHV and GS when varying the number of offspring per cross (nOff) (10, 50, 100, 200, 500, and 1000) using heterotic group 1 SNP effects in an empirical marker set from maize. Range of standard error from 0.04 to 0.11.
Figure 18:
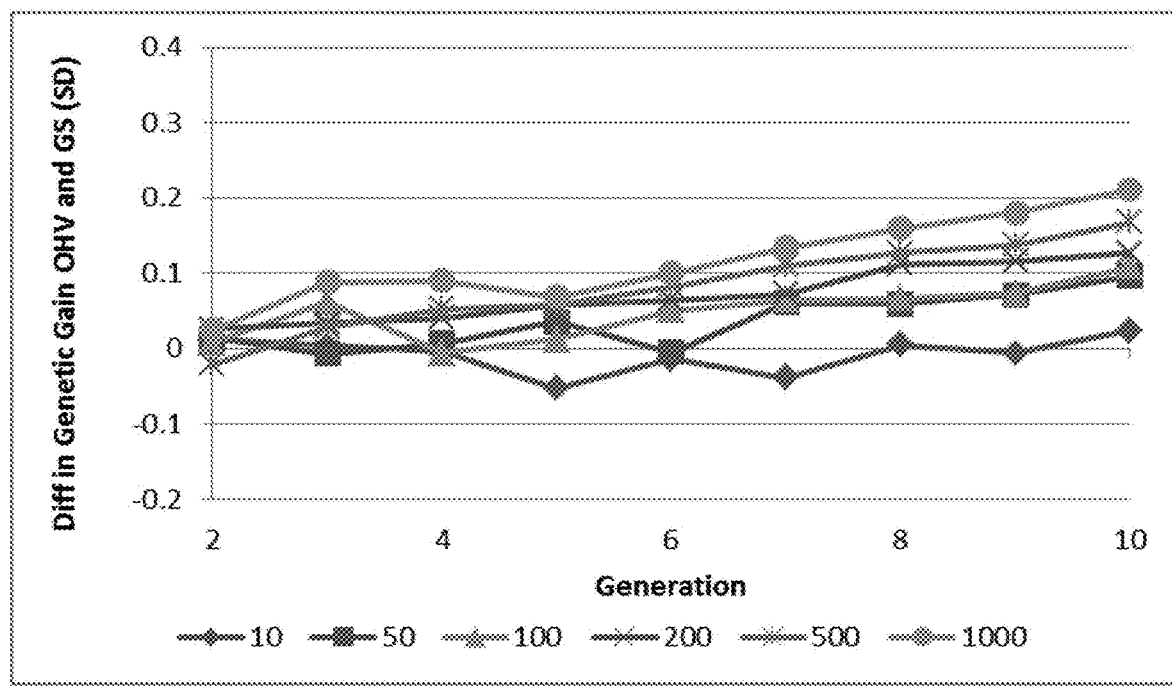
FIG. 18 includes a graphical representation illustrating the difference in genetic gain per generation between OHV and GS when varying the number of doubled haploids produced per elite plant (nDH) 10, 50, 100, 200, 500, and 1000) using heterotic group 1 SNP effects in an empirical marker set from maize. Range of standard error from 0.04 to 0.08.
Figure 19:
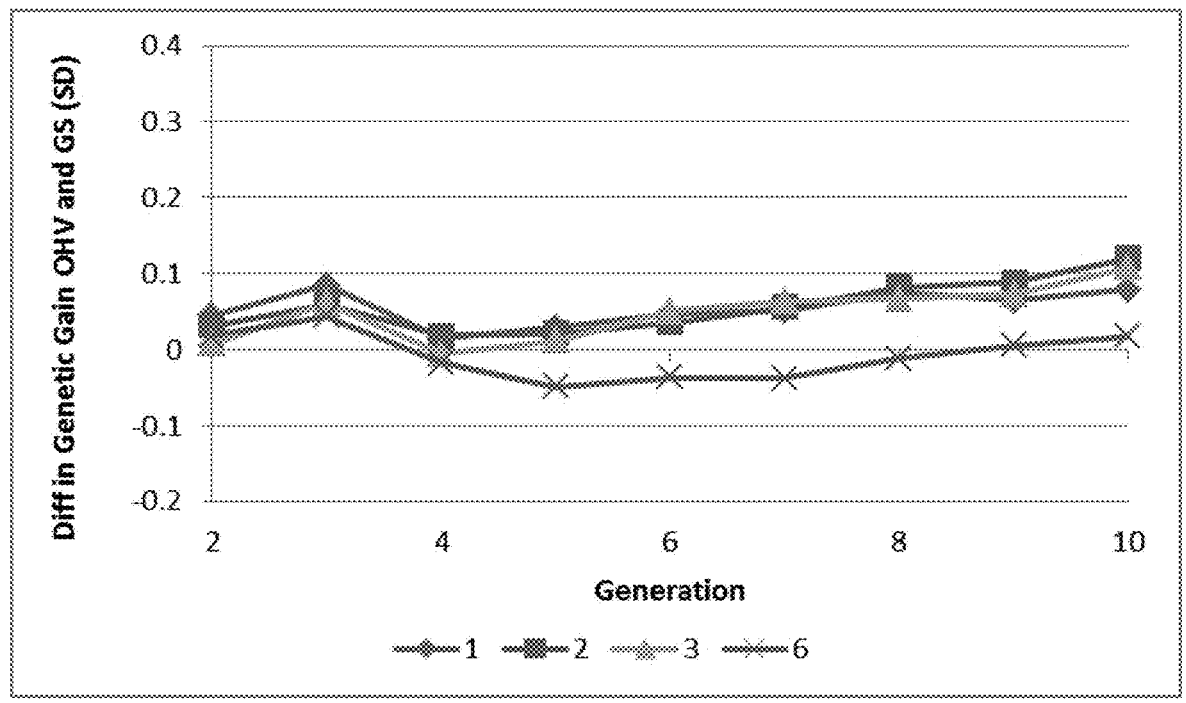
FIG. 19 includes a graphical representation illustrating the difference in genetic gain per generation between OHV and GS when varying the number of haplotype segments per chromosome (nSeg) (1, 2, 3, and 6) using heterotic group 2 SNP effects in an empirical marker set from maize. Range of standard error from 0.03 to 0.08.
Figure 20:
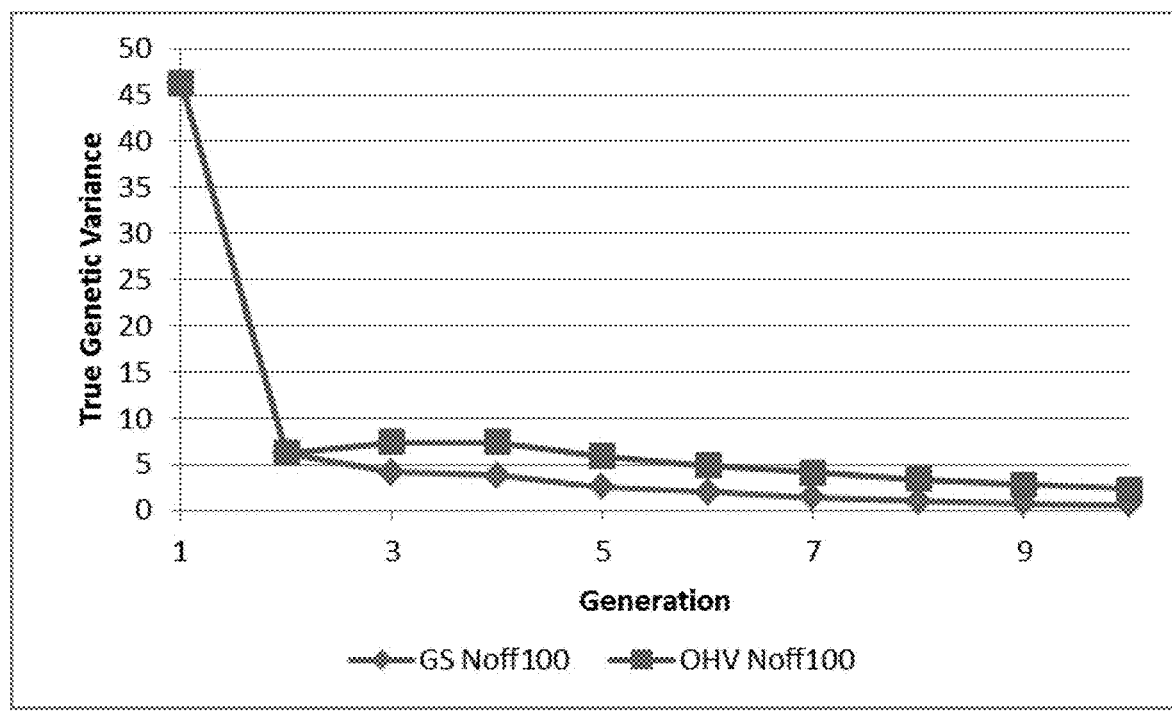
FIG. 20 includes a graphical representation illustrating the true genetic variance per generation of OHV and GS breeding programs and using heterotic group 2 SNP effects in an empirical marker set from maize. Range of standard error from 0.0 to 0.11.

In general, OHV selection yielded increased genetic gain relative to genomic selection when using Group 1 SNP effects and there was an upward trend for this difference in later generations. The difference between GS and OHV was smaller than in stream 1. Results for the same scenarios as stream 1 are presented in FIGS. 13-16. In these simulations, empirical SNP effects seemed to decrease the genetic variance proportionally more than sampling effects. See FIG. 16. However, OHV selection still maintained more genetic diversity than genomic selection. Using the effects in group 2 in the simulations again confirmed the relative advantages of OHVs over GS. See FIGS. 17-20. The difference between OHV and GS was smaller in these scenarios but still showed a slight advantage for OHV.

The results in this study confirm that OHV selection increases genetic gain and maintains more genetic diversity in breeding populations when compared to genomic selection. The maize analysis in stream 1 showed a larger benefit of OHV (compared to the wheat study herein) which differed by species, the number of chromosomes, and the number of SNP. In stream 1, 23,880 SNPs were available as compared to approximately 5,000 SNPs in wheat. Aside from species, the increased advantage in the current analyses could be due to the increased SNP number, which may facilitate a more accurate targeting of haplotypes.

The results from stream 2 confirmed those of stream 1, although the increase of OHV over GS was lower and the signal was much stronger in stream 1. This may be due to the use of empirical SNP effects that were regressed back towards the mean, reflecting a relatively small reference population used to estimate the effects, and the estimation method used. With a larger reference, the advantage of OHV could be greater (as suggested by the simulation results). Regression towards the mean reduces differences between SNP effects and therefore reduces the efficiency of selection for both GS and OHV.

In all three groups of analyses, OHV selection maintained substantially more genetic diversity in the breeding population. This confirms that with OHV selection genetic gain is possible while keeping a greater genetic variance in the population to achieve genetic gain in the future.

Example 5: Combining OHV and Epistasis

The number of epistatic effects to be estimated in a breeding program is drastically reduced using the methodology of calculating the epistatic effects within a haplotype only, and subsequently adding the effects to the OHV value to produce an additive OHVe value. Table 12. The extent of the reductions range from 1.5% to 0.2% of the original 16.2 billion interactions to test, while still exploring the interactions with the highest likelihood across the genome.

large genomic reference populations that are genotyped and phenotypically characterized. Starting with the estimation of epistatic effects across segments first, which are significantly less than loci interactions within segments, effectively prioritizes epistatic effects to a more useful interaction space. The number of epistatic interactions to be tested is further reduced by evaluating interactions at longer genomic distances by testing interactions of the most common haplotypes of segments.

The inclusion of epistatic effects thus allows for the selection of favorable interactions and genetic backgrounds in plant breeding.

Example 6: Accelerated Breeding of the Optimal Plant

Instead of randomly mating the parents in the foregoing schemes, a mating scheme is devised that combines parents with strengths (or desired traits) in different genome segments to increase the probability of offspring carrying segments with all of the desired genome segments. The haplotype composition of the ideal plant is generated in silico, and a breeding scheme is devised to attain it. Such a breeding scheme is then carried out, leading to the development of a plant having a CHV that approaches the OHV. This breeding scheme accelerates breeding of plants with multiple desirable strengths or traits.

What may be claimed is:

1. A method for providing increased genetic gain and maintaining genetic diversity in a progeny plant population, the method comprising:

haplotyping each plant of two or more initial plants for a plurality of individual haploid genome segments, wherein each initial plant comprises a polyploid genome and each haploid genome segment has a haploid value (HV) for the one or more traits of interest and the sum of all HVs in an individual plant's haploid genome is the combined haploid value (CHV) for that individual plant;

TABLE 12

The number of interactions to be tested using various ways to prioritize which interactions to test assuming 90,000 SNP markers and 21 chromosomes, where segments refers to the number of OHV segments in total across the wheat genome.

|  | Number of Interactions | | | | |
| --- | --- | --- | --- | --- | --- |
|  | No. Segments | Segments Within | Segments Across | Total | % of testing all |
| No segments, testing all | 16,199,820,000 | — | — | 16,199,820,000 | — |
| 63 segments, 10 common haplotypes | — | 256,962,857 | 198,135 | 257,160,992 | 1.6% |
| 210 segments, 10 common haplotypes | — | 76,962,857 | 2,203,950 | 79,166,807 | 0.5% |
| 630 segments, 10 common haplotypes | — | 25,534,286 | 19,841,850 | 45,376,136 | 0.3% |
| 63 segments, 5 common haplotypes | — | 256,962,857 | 49,455 | 257,012,312 | 1.6% |
| 210 segments, 5 common haplotypes | — | 76,962,857 | 550,725 | 77,513,582 | 0.5% |
| 630 segments, 5 common haplotypes | — | 25,534,286 | 4,959,675 | 30,493,961 | 0.2% |

There is an optimum number of OHV segments that reduces the number of interactions to test within a segment will still keeping the number of across segment epistatic effects manageable. However, even with the lowest number of total epistatic effects to test at 30.5 million, it is still a significant statistical and computational challenge requiring crossing one of the haplotyped initial plants (a first initial parental plant) with a second haplotyped initial plant (a second initial parental plant) to produce a progeny plant population;

determining an optimal haploid value (OHV) that is the sum of the highest HVs for each haploid genome segment in the first initial parental and second initial parental plants and OHV is the highest CHV obtainable in the progeny plant population from the plurality of genome segments in the first initial parental plant and second initial parental plant;

haplotyping plants of the progeny plant population and determining the CHV of the haplotyped progeny plants;

selecting at least one progeny parental plant from the progeny plant population, wherein each selected progeny parental plant has a CHV that is higher and closer to the OHV than the CHVs of the progeny plants that are not selected; and crossing each selected progeny parental plant with another plant to thereby produce a next generation progeny plant population.

2. The method according to claim 1, wherein the method comprises one or more additional rounds of selection and crossing of plants from next generation progeny plant populations, such that each additional round of selection and crossing comprises:

(a) haplotyping plants of the next generation of progeny plant population and determining the CHV of the haplotyped progeny plants, (b) selecting at least one plant from the next generation progeny plant population to be a next generation parental plant, wherein the CHV of the selected next generation plant is higher and closer to the OHV than the CHV of next generation progeny plants that are not selected; and (c) crossing each selected next generation parental plant with another plant to thereby produce a further next generation progeny plant population.

3. The method according to claim 2, wherein the method further comprises repeating steps (a), (b), and (c) at least two times, such that the method includes at least three rounds of selection and crossing of next generation progeny plants.

4. The method according to claim 2, wherein the method further comprises repeating steps (a), (b), and (c) at least four times, such that the method includes at least five rounds of selection and crossing of next generation progeny plants.

5. The method according to claim 1, wherein haplotyping each plant of an initial plant population for a plurality of individual haploid segments of the initial plant genome comprises amplification of genomic DNA from the plants by polymerase chain reaction (PCR), and hybridization of allele-specific oligonucleotide probes.

6. The method according to claim 1, wherein the initial plant population is segregating for the trait of interest.

7. The method according to claim 1, wherein the genome of the plants of the initial plant population is a diploid genome.

8. The method according to claim 1, wherein the combination of all of the individual haploid segments covers the entire plant genome.

9. The method according to claim 1, wherein the individual haploid segments are between 10 cM and 50 cM in length, or fragments generated by restriction digestion of genomic DNA with one or more nucleases.

10. The method according to claim 1, wherein each selected progeny parental plant has a CHV that is at least 80% of the OHV.

11. The method according to claim 1, wherein each selected progeny parental plant has a CHV that is at least 90% of the OHV.

12. The method according to claim 4, wherein at least one selected next generation parental plant has a CHV that is at least 95% of the OHV.

13. The method according to claim 1, wherein the first initial and second initial parental plants are individuals in a breeding population and crossing the first initial parental plant and the second initial parental plant provides a higher OHV than the OHV of progeny that would be produced by crossing the first initial parental plant with a plant in the breeding population that is not the second initial parental plant.

14. The method according to claim 1, wherein the first initial and second initial parental plants are individuals in a breeding population and crossing the first initial parental plant and the second initial parental plant provides the highest OHV possible among available crosses of plants in the breeding population.

15. The method according to claim 14, wherein the first initial parental plant satisfies a further selection criteria, and the second initial parental plant does not satisfy the further selection criteria.

16. The method according to claim 15, wherein the further selection criteria is the presence of a genetic marker of interest.

17. The method according to claim 16, wherein the genetic marker of interest is an allele or transgenic event.

18. The method according to claim 15, wherein the method comprises propagating the plant that has the highest CHV in the next generation progeny plant population that also comprises the genetic marker of interest.

19. The method according to claim 1, wherein the method comprises producing haploid plant materials from plants of the progeny plant population, wherein the haploid plant materials are haploid plants or haploid plant tissues.

20. The method according to claim 19, wherein the method further comprises propagating a doubled haploid plant produced from a haploid plant material having a combined haploid value (CHV) that is at least 80% of the OHV.

21. The method according to claim 19, wherein the method further comprises selfing a doubled haploid plant produced from a haploid plant material having a combined haploid value (CHV) that is at least 80% of the OHV.

22. The method according to claim 20, wherein the method comprises crossing the doubled haploid plant with one of the first initial parental and second initial parental plants.

23. The method according to claim 1, wherein each selected next generation parental plant does not have the highest average genomic estimated breeding values (GEBV) of the plants in the progeny plant population.

* * * * *